(12) United States Patent
Thakur et al.

(10) Patent No.: US 11,541,242 B2
(45) Date of Patent: Jan. 3, 2023

(54) SYSTEMS AND METHODS FOR HEART FAILURE MANAGEMENT

(71) Applicant: Cardiac Pacemakers, Inc., St. Paul, MN (US)

(72) Inventors: Pramodsingh Hirasingh Thakur, Woodbury, MN (US); Jason Humphrey, New Brighton, MN (US); David J. Ternes, Roseville, MN (US); Qi An, Blaine, MN (US); Krzysztof Z. Siejko, Maple Grove, MN (US); Michael James Dufresne, Lino Lakes, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1085 days.

(21) Appl. No.: 16/114,375

(22) Filed: Aug. 28, 2018

(65) Prior Publication Data

US 2019/0083789 A1    Mar. 21, 2019

Related U.S. Application Data

(60) Provisional application No. 62/561,175, filed on Sep. 20, 2017.

(51) Int. Cl.
*A61N 1/36* (2006.01)
*A61N 1/365* (2006.01)
(Continued)

(52) U.S. Cl.
CPC ........ *A61N 1/36585* (2013.01); *A61B 5/7275* (2013.01); *A61B 5/7282* (2013.01);
(Continued)

(58) Field of Classification Search
CPC . A61B 5/02028; A61B 5/7282; A61B 5/7275; A61B 7/02–04; A61N 1/365;
(Continued)

(56) References Cited

U.S. PATENT DOCUMENTS 5,836,987 A * 11/1998 Baumann ........... A61N 1/36542
607/18
7,853,327 B2   12/2010 Patangay et al.
(Continued)

FOREIGN PATENT DOCUMENTS

CN       111093758 A    5/2020
WO    WO-2019060100 A1  3/2019

OTHER PUBLICATIONS

De Tombe, Pieter P., "Altered contractile function in heart failure", Cardiovascular Research 37, 367-380 (1998).
(Continued)

*Primary Examiner* — Unsu Jung
*Assistant Examiner* — Natasha Patel
(74) *Attorney, Agent, or Firm* — Schwegman Lundberg & Woessner, P.A.

(57) ABSTRACT

Systems and methods for managing heart failure are described. The system receives physiological information including a first HS signal corresponding to paced ventricular contractions and a second HS signal corresponding to intrinsic ventricular contractions. The system detects worsening heart failure (WHF) using the received physiological information. A signal analyzer circuit can generate a paced HS metric from the first HS signal and a sensed HS metric from the second HS signal, and determine a concordance indicator between the paced and the sensed HS metrics. In response to the detected WHF, the system can use the concordance indicator to generate a therapy adjustment indicator for adjusting electrostimulation therapy, or a wors- (Continued)

ening cardiac contractility indicator indicating the detected WHF is attributed to degrading myocardial contractility.

20 Claims, 7 Drawing Sheets

(51) Int. Cl.
*A61N 1/362* (2006.01)
*A61B 5/00* (2006.01)
*A61N 1/37* (2006.01)
*A61N 1/39* (2006.01)
*A61N 1/368* (2006.01)
A61B 5/0205 (2006.01)
A61M 60/148 (2021.01)

(52) U.S. Cl.
CPC ......... *A61N 1/3627* (2013.01); *A61N 1/3682* (2013.01); *A61N 1/3684* (2013.01); *A61N 1/36514* (2013.01); *A61N 1/3702* (2013.01); *A61N 1/3962* (2013.01); *A61B 5/0205* (2013.01); *A61M 60/148* (2021.01); *A61M 2205/3303* (2013.01); *A61M 2205/3375* (2013.01); *A61M 2205/502* (2013.01); *A61M 2230/04* (2013.01)

(58) Field of Classification Search
CPC ............ A61N 1/36514; A61N 1/36585; A61N 1/3702
See application file for complete search history.

(56) References Cited

U.S. PATENT DOCUMENTS

| | | | |
|---|---|---|---|
| 2002/0151938 A1* | 10/2002 | Corbucci | A61N 1/3684 607/25 |
| 2004/0106960 A1* | 6/2004 | Siejko | A61N 1/3684 607/17 |
| 2004/0267086 A1* | 12/2004 | Anstadt | A61M 60/50 600/17 |
| 2005/0137631 A1 | 6/2005 | Yu et al. | |
| 2009/0054942 A1* | 2/2009 | Zhu | A61N 1/3627 607/11 |
| 2012/0296228 A1 | 11/2012 | Zhang et al. | |
| 2014/0275925 A1 | 9/2014 | Thakur et al. | |
| 2014/0277238 A1* | 9/2014 | An | A61N 1/3682 607/18 |
| 2014/0277243 A1* | 9/2014 | Maskara | A61N 1/36578 607/28 |
| 2015/0157260 A1 | 6/2015 | Zhang et al. | |
| 2015/0342466 A1 | 12/2015 | Thakur et al. | |
| 2016/0030747 A1* | 2/2016 | Thakur | A61N 1/3686 607/18 |
| 2016/0106987 A1 | 4/2016 | An et al. | |
| 2017/0095160 A1 | 4/2017 | Thakur et al. | |
| 2017/0113052 A1* | 4/2017 | An | A61N 1/37264 |

OTHER PUBLICATIONS

Gheorghiade, Mihai, "The Pilot Randomized Study of Nesiritide Versus Dobutamine in Heart Failure", The American Journal of Cardiology; 96, (6A), (Sep. 19, 2005), 18G-25G.
Peacock IV, W. Frank, et al., "Cardiac Troponin and Outcome in Acute Heart Failure", N Engl J Med., 358:2117-2126, 2008.
"European Application Serial No. 18766479.2, Response to Communication Pursuant to Rules 161 and 162 EPC filed Oct. 8, 2020", 20 pgs.
"International Application Serial No. PCT/US2018/048246, International Preliminary Report on Patentability dated Apr. 2, 2020", 8 pgs.
"International Application Serial No. PCT/US2018/048246, International Search Report dated Nov. 12, 2018", 5 pgs.
"International Application Serial No. PCT/US2018/048246, Written Opinion dated Nov. 12, 2018", 6 pgs.

* cited by examiner

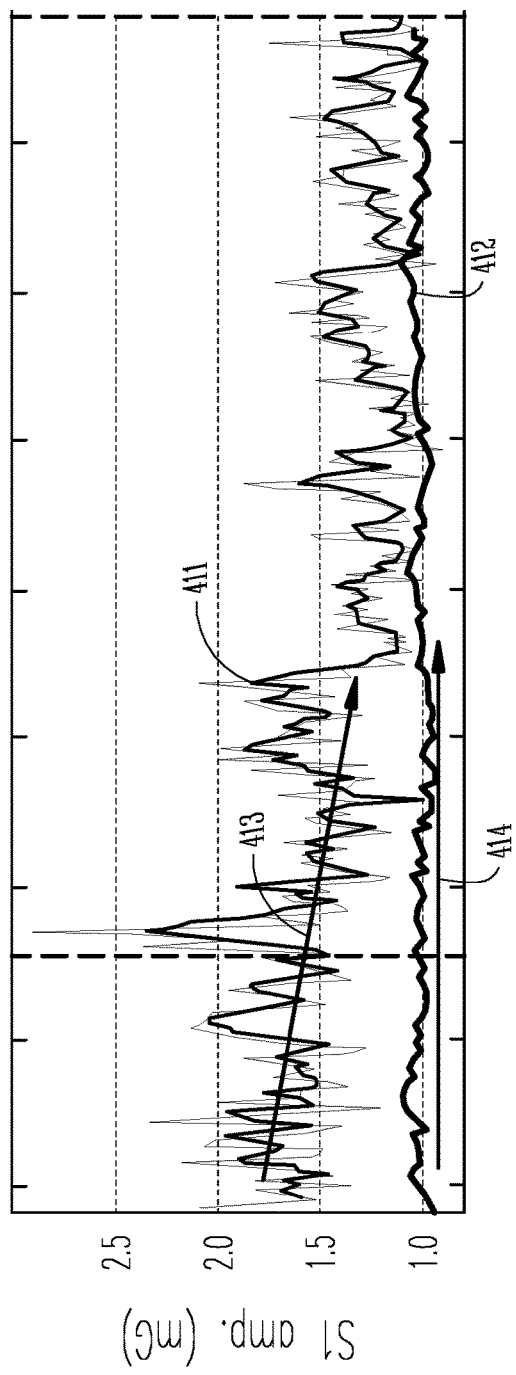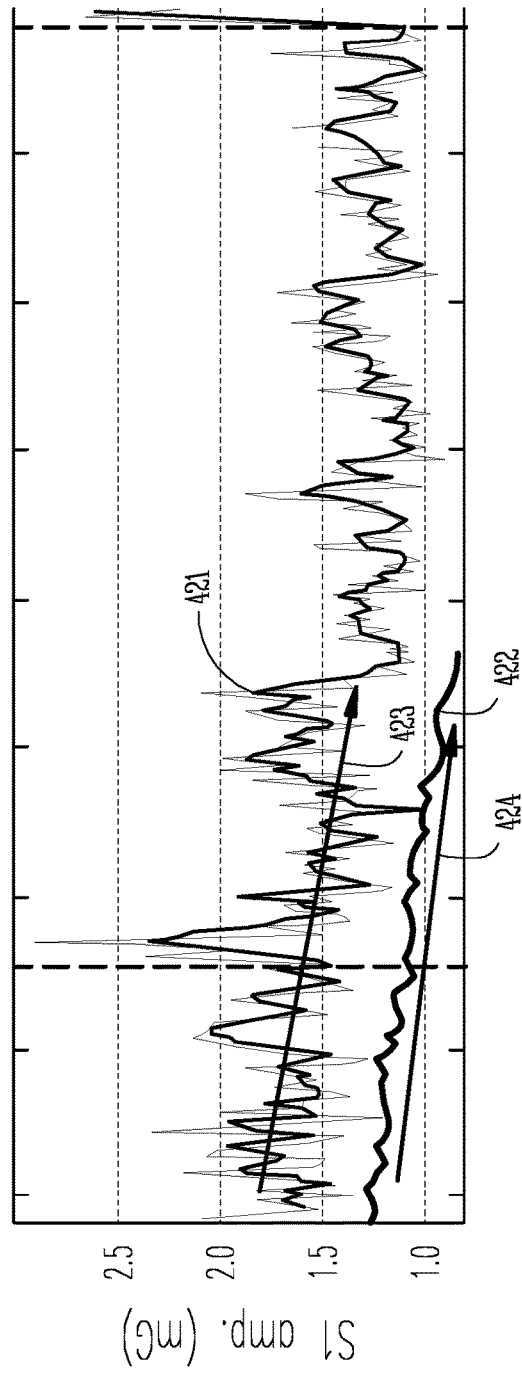

SYSTEMS AND METHODS FOR HEART FAILURE MANAGEMENT

CLAIM OF PRIORITY

This application claims the benefit of priority under 35 U.S.C. § 119(e) of U.S. Provisional Patent Application Ser. No. 62/561,175, filed on Sep. 20, 2017, which is herein incorporated by reference in its entirety.

TECHNICAL FIELD

This document relates generally to medical systems, and more particularly, to systems, devices and methods for monitoring patients with a heart failure.

BACKGROUND

Congestive heart failure (CHF or HF) is a major health problem and affects many people in the United States and globally. CHF occurs when the heart is unable to supply enough blood to maintain a healthy physiological state. CHF may be treated by drug therapy, or by an implantable medical device (IMD) that may provide electrostimulation therapy.

Sonic IMDs can sense physiological signals from a patient via electrodes or sensors, and detect events leading to worsening heart failure (WHF). Frequent CHF monitoring and timely detection of WHF events may help reduce healthcare cost associated with HF hospitalization. Identification of patient at an elevated risk for future WHF events may help ensure timely treatment, improve the prognosis and patient outcome, and avoid unnecessary medical interventions, and save the overall cost.

Some IMDs have an electronics unit such as a pulse generator that can generate electrostimulation for chronically stimulating excitable tissues or organs, such as a heart. The electrostimulation can help restore or improve cardiac performance, or rectify abnormal cardiac rhythms in a CHF patient. One example of electrostimulation therapy is resynchronization therapy (CRT). CRT involves electrostimulation of both left and right ventricles, which keeps both ventricles pumping synchronously. CRT may improve the pumping efficiency and increases blood flow in some CHF patients.

OVERVIEW

An ambulatory medical device (AMD), such as an implantable medical device, a subcutaneous medical device, a wearable medical device, or other external medical device, may be used to monitor CHF patient and deliver device therapy to restore or improve patient cardiac function. The AMD may include sensors to sense physiological signals, such as heart sounds (HS). HS can be associated with mechanical vibrations of the heart and the blood flow through the heart, and contain information about cardiac systolic and diastolic functions. Systole is the contraction or a period of contraction of the heart that causes blood to be forced out of the heart. Diastole is the relaxation or a period of relaxation of the heart during which the blood flows back into the heart.

HS recurs with each cardiac cycle and are separated and classified according to the activity associated with the vibration. Typically, HS sensed from a subject may include several components within a cardiac cycle, including one or more of a first (S1), a second (S2), a third (S3), or a fourth (S4). S1 is associated with the vibrational sound made by the heart during tensing of the mitral valve. S2 is produced by closure of the aortic and pulmonary valves, and marks the beginning of diastole. S3 is an early diastolic sound corresponding to passive ventricular filling during diastole, when the blood rushes into the ventricles. S4 is a late diastolic sound corresponding to active ventricular filling when the atria contract and push the blood into the ventricles. S3 is usually faint and S4 is rarely audible in a healthy subject. A pathologic S3 or S4 may be higher pitched and louder.

Heart sounds may be used to assess patient HF status. HF patient may have fluid accumulation in the lungs, which may cause elevated ventricular filling pressure. WHF may be accompanied by diastolic dysfunction, resulting in pathologically louder S3. Profound. S4 may also be present in CHF patients due to forceful atrial contraction to overcome an abnormally stiff ventricle. Therefore, S3 or S4 may be used to qualify diastolic dysfunction and to detect WHF. Additionally, some patients experiencing WHF may have reduced S1 amplitude. S1 amplitude has been found to be correlated with myocardial contractility. Patient hospitalized for WHF may have a deteriorated systolic function with poor contractility. Therefore, a progressive decrease in S1 amplitude may indicate worsening of HF status.

An AMD may electrically stimulate cardiac tissue or other excitable tissue to restore or improve cardiac function. CRT is a type of cardiac electrostimulation therapy that may be delivered to both ventricles, known as biventricular (BiV) pacing. Alternatively, electrostimulation may be delivered only to the left ventricle (LV), known as LV-only pacing. Some AMDs are capable of stimulating multiple sites of a heart chamber (e.g., left ventricle). In contrast to conventional single site pacing (SSP) which involves electrostimulation of only one site of a heart chamber (e.g., the LV), multisite pacing (MSP) involves electrostimulation of two or more sites in a heart chamber simultaneously or sequentially within a cardiac cycle. For example, in a LV MSP, multiple LV sites can be stimulated simultaneously or separated by intra-LV time offsets. MSP may improve LV function and hemodynamic responses in some patients. In an example, the cardiac electrostimulation may include pacing of a target portion of a conductive tissue of the heart such as His bundle, or pacing at excitable cardiac tissue for modulating cardiac contractility. An AMD may sense a physiological signal during cardiac electrostimulation, and assess cardiac function and detect WHF using the sensed physiological signal. In an example, the AMD may sense the physiological signal during neural stimulation, such as vagus nerve stimulation, spinal cord stimulation, or baroreceptor stimulation, among other neuromodulations. In an example, an AMD may sense HS during cardiac or neural stimulation, and detect a reduction in S1 amplitude that is indicative of pathological remodeling and reduction in myocardial contractility. The AMD may detect WHF using the HS corresponding to the pacing therapy.

Although HS information such as reduced S1 amplitude during cardiac electrostimulation may represent deteriorated myocardial contractility associated with WHF, such HS characteristics may not be specific to reduced myocardial contractility in some patients. For example, reduced S1 amplitude may also be attributed to ineffective cardiac electrostimulation even when the patient has preserved myocardial contractile function. Stimulation sites (e.g., positions of stimulation electrode in or on a heart), stimulation modes (e.g., LV-only pacing, BiV pacing, or multisite pacing), or stimulation parameters (e.g., timing, or energy of stimulation pulses delivered to the heart) may individually or jointly affect the therapy effectiveness. A less effective cardiac electrostimulation may also result in changes in HS, such as reduced S1 amplitude. The present inventors have recognized that a proper identification of the cause of characteristic HS changes, such as reduced S1 amplitude, may not only provide useful diagnostic about patient HF status, but may also guide appropriate treatment and patient management options.

Embodiments of the present subject matter provide systems, devices, and methods for managing heart failure using HS. A system may receive physiological information including a first HS signal corresponding to ventricular pacing and a second HS signal in the absence of ventricular pacing, such as corresponding to intrinsic ventricular contractions. The system may detect worsening heart failure (WHF) using the received physiological information. A signal analyzer circuit may generate a paced HS metric from the first HS signal and a sensed HS metric from the second HS signal, and determine a concordance indicator between the paced and the sensed HS metrics. In response to the detected WHF and using the concordance indicator, the system may generate a therapy adjustment indicator for adjusting electrostimulation therapy, or a worsening cardiac contractility indicator indicating the detected WHF is attributed to degrading myocardial contractility.

Example 1 is a system, comprising a receiver circuit and a heart failure detector and analyzer circuit. The receiver circuit may receive physiological information including a first heart sound (HS) signal corresponding to paced ventricular contractions and a second HS signal corresponding to intrinsic ventricular contractions. The heart failure detector and analyzer circuit may generate (1) a paced HS metric from the first HS signal and (2) a sensed HS metric from the second HS signal, and determine a worsening heart failure indicator based on the paced HS metric and the sensed HS metric. The paced HS metric indicates cardiac contractility in response to paced ventricular contractions. The sensed HS metric indicates cardiac contractility in response to intrinsic ventricular contraction.

In Example 2, the subject matter of Example 1 optionally includes an output circuit that may generate a worsening cardiac contractility indicator using a concordance between the paced and the sensed. HS metrics.

In Example 3, the subject matter of Example 2 optionally includes the heart failure detector and analyzer circuit that may trend the paced HS metric and trend the sensed HS metric over time, and determine the concordance using the paced HS metric trend relative to the sensed HS metric trend.

In Example 4, the subject matter of Example 3 optionally includes the concordance that may include a correlation between the paced HS metric trend and the sensed HS metric trend. The output circuit may generate a therapy adjustment indicator when the correlation satisfies a first condition, and generate the worsening cardiac contractility indicator when the correlation satisfies a different second condition.

In Example 5, the subject matter of Example 3 optionally includes the concordance including a HS ratio of a temporal change of the sensed HS metric to a temporal change of the paced HS metric. The output circuit may generate a therapy adjustment indicator when the HS ratio satisfies a first condition, and generate the worsening cardiac contractility indicator when the HS ratio satisfies a different second condition.

In Example 6, the subject matter of any one or more of Examples 1-5 optionally include the heart failure detector and analyzer circuit that may generate the paced HS metric including measure a paced first sound (S1) intensity from the first HS signal during ventricular pacing, and generate the sensed HS metric including measure a sensed S1 intensity from the second HS signal in the absence of ventricular pacing.

In Example 7, the subject matter of Example 6 optionally includes the heart failure detector and analyzer circuit that may determine a pacing effectiveness indicator using the paced S1 intensity relative to the sensed S1 intensity.

In Example 8, the subject matter of any one or more of Examples 1-7 optionally includes the heart failure detector and analyzer circuit that may generate the paced HS metric including measure a paced cardiac timing interval (CTI) using the first HS signal during ventricular pacing, and generate the sensed HS metric including measure a sensed CTI using the second HS signal in the absence of ventricular pacing.

In Example 9, the subject matter of Example 8 optionally includes the CTI that may include at least one of a pre-ejection period or a ventricular ejection time interval.

In Example 10, the subject matter of any one or more of Examples 2-9 optionally includes an electrostimulator circuit that may deliver cardiac pacing according to one or more pacing parameters. The output circuit may generate a therapy adjustment indicator for adjusting at least one of the one or more pacing parameters using the concordance between the paced and the sensed HS metrics.

In Example 11, the subject matter of Example 10 optionally includes the electrostimulator circuit that may deliver ventricular pacing. The output circuit may generate the therapy adjustment indicator for adjusting timing of ventricular pacing using the concordance between the paced and the sensed HS metrics.

In Example 12, the subject matter of any one or more of Examples 10-11 optionally includes HS sensor circuit that may sense the first HS signal when the electrostimulator circuit delivers ventricular pacing, and sense the second HS signal when the electrostimulator circuit withholds ventricular pacing.

In Example 13, the subject matter of any one or more of Examples 2-12 optionally include the heart failure detector and analyzer circuit that may generate (1) a first paced HS metric from a first portion of the first HS signal corresponding to paced atrial contractions, and (2) a second paced HS metric from a different second portion of the first HS signal corresponding to intrinsic atrial contractions. The output circuit may generate a therapy adjustment indicator for adjusting one or more of timing of ventricular pacing relative to the atrial pacing, or timing of ventricular pacing relative to the intrinsic atrial contractions.

In Example 14, the subject matter of any one or more of Examples 2-13 optionally includes the heart failure detector and analyzer circuit that may determine a pacing capture status using the first HS signal. The output circuit may generate a therapy adjustment indicator for adjusting the electrostimulation therapy using the determined pacing capture status.

In Example 15, the subject matter of Example 14 optionally includes a user interface that may display one or more of a trend of the intensity of the paced S1, a trend of the intensity of the sensed S1, or a trend of the pacing effectiveness indicator.

Example 16 is a system, comprising a receiver circuit, a heart failure detector and analyzer circuit, and a control circuit. The receiver circuit may be configured to receive physiological information including a first heart sound (HS) signal corresponding to paced ventricular contractions and a second HS signal corresponding to intrinsic ventricular contractions. The heart failure detector and analyzer circuit may be configured to generate (1) a paced HS metric from the first HS signal and (2) a sensed HS metric from the second HS signal, the paced HS metric indicating cardiac contractility in response to paced ventricular contractions, the sensed HS metric indicating cardiac contractility in response to intrinsic ventricular contractions. The control circuit may be configured to adjust a therapy delivered to a patient based on the paced HS metric and sensed HS metric.

In Example 17, the subject matter of Example 16 optionally includes the control circuit is configured to display information corresponding to the paced HS metric and the sensed HS metric, and to receive a therapy adjustment for adjusting the therapy provided to the patient.

Example 18 is a method for adjusting a heart failure therapy using a medical system. The method comprises steps of receiving physiological information via a receiver circuit, the physiological information including a first heart sound (HS) signal corresponding to a paced ventricular contractions and a second HS signal corresponding to intrinsic ventricular contractions; generating (1) a paced HS metric from the first HS signal and (2) a sensed HS metric from the second HS signal via the heart failure detector and analyzer circuit, the paced HS metric indicating cardiac contractility in response to paced ventricular contractions, the sensed HS metric indicating cardiac contractility in response to intrinsic ventricular contractions; determining a worsening heart failure indicator using the paced HS metric and the sensed HS metric via the heart failure detector and analyzer circuit.

In Example 19, the subject matter of Example 18 optionally includes generating a worsening cardiac contractility indicator using a concordance between the paced and the sensed HS metrics.

In Example 20, the subject matter of Example 19 optionally includes determining the concordance using a HS ratio of a temporal change of the sensed HS metric to a temporal change of the paced HS metric.

In Example 21, the subject matter of Example 18 optionally includes generating the paced HS metric that may include measuring a paced first sound (S1) intensity from the first HS signal during ventricular pacing, and generating the sensed HS metric includes measuring a sensed S1 intensity from the second HS signal in the absence of ventricular pacing.

In Example 22, the subject matter of Example 18 optionally includes generating the paced HS metric that may include measuring a paced cardiac timing interval (CTI) using the first HS signal during ventricular pacing, and generating the sensed HS metric includes measuring a sensed CTI using the second HS signal in the absence of ventricular pacing.

In Example 23, the subject matter of Example 18 optionally includes adjusting one or more pacing parameters using the concordance between the paced and the sensed HS metrics, and delivering cardiac pacing according to the adjusted one or more pacing parameters.

In Example 24, the subject matter of Example 18 optionally includes generating (1) a first paced HS metric from a first portion of the first HS signal corresponding to paced atrial contractions, and (2) a second paced HS metric from a different second portion of the first HS signal corresponding to intrinsic atrial contractions, and generating a therapy adjustment indicator for adjusting one or more of timing of ventricular pacing relative to the atrial pacing, or timing of ventricular pacing relative to the intrinsic atrial contractions.

The systems, devices, and methods discussed in this document may improve the technology of device-based heart failure management. The present document provides a technological solution to a technical challenge of identifying the causes of reduced benefit of device therapy in certain patients, such as insufficient improvement of cardiac functionality and hemodynamics provided by the CRT or other electrostimulation therapies. The technology discussed in the present document differentially identifies the WHF as being attributed to reduced myocardial contractility, or attributed to sub-optimal device programming (but with preserved myocardial contractility). The identification may be based on characteristic changes in HS metrics when the heart undergoes ventricular pacing and characteristic changes in HS metrics in the absence of ventricular pacing, such as during intrinsic ventricular contractions. Ventricular pacing may include epicardial or endocardial pacing of a ventricle, or pacing at a portion of the electrical conduction system of the heart such as the His bundle. Such an identification is advantageous, as it may assist a clinician to choose more appropriate and individualized therapies or interventions tailored to specific patient conditions, yet at little to no additional cost or system complexity. For example, if the reduced S1 amplitude is determined to be resulted from ineffective cardiac electrostimulation, then re-programming of device therapy (e.g., CRT, multisite pacing, His bundle pacing, or neurostimulation) may effectively activate viable cardiac tissues with preserved myocardial contractility, and rectify the WHF and improve patient cardiac function. However, if the reduced S1 amplitude is determined to be a result of pathological remodeling and reduction in myocardial contractility, then medical therapies such as inotropic agents may be administered to bolster myocardial contractility, because mere reprogramming of pacing therapy may not achieve desired therapeutic benefits. With proper identification of the causes of reduced device therapy benefit, fewer unnecessary medical interventions, such as drugs, procedures, or device therapies, may be scheduled, prescribed, or provided to such patients. As a result, better patient outcome and overall system cost savings may be realized.

The identification of the causes of reduced benefit of device therapy or the detected WHF, as discussed in this document, may also improve the functionality of a patient management system or an AMD. In some cases, such an identification may be achieved without a modification of existing patient AMDs. Memory usage may be more efficient by storing HS information clinically more relevant to medical diagnosis and therapy, such as HS metrics during ventricular pacing and HS metrics corresponding to intrinsic ventricular contractions. The therapy adjustment indicator and worsening cardiac contractility indicator, which may be used to guide therapy, requires limited memory space and transmission bandwidth. Timely identification of the reduced benefit of device therapy as being attributed to the reduced myocardial contractility may help reduce unnecessary device therapies, thus extend battery life and AMD longevity.

Although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 4A-B illustrate examples of S1 amplitude trends in the presence or absence of ventricular pacing when patient HF status worsens.

DETAILED DESCRIPTION

Disclosed herein are systems, devices, and methods for managing heart failure. The system receives physiological information from a patient, including a first HS signal corresponding to paced ventricular contractions and a second HS signal corresponding to intrinsic ventricular contractions. A paced HS metric may be generated from the first HS signal and a sensed HS metric may be generated from the second HS signal. The system may detect worsening heart failure (WHF) using the received physiological information, and determine a concordance indicator between the paced and the sensed HS metrics. In response to the detected WHF, the system may use the concordance indicator to generate a therapy adjustment indicator for adjusting electrostimulation therapy, or a worsening cardiac contractility indicator indicating the detected WHF is attributed to degrading myocardial contractility.

Figure 1:
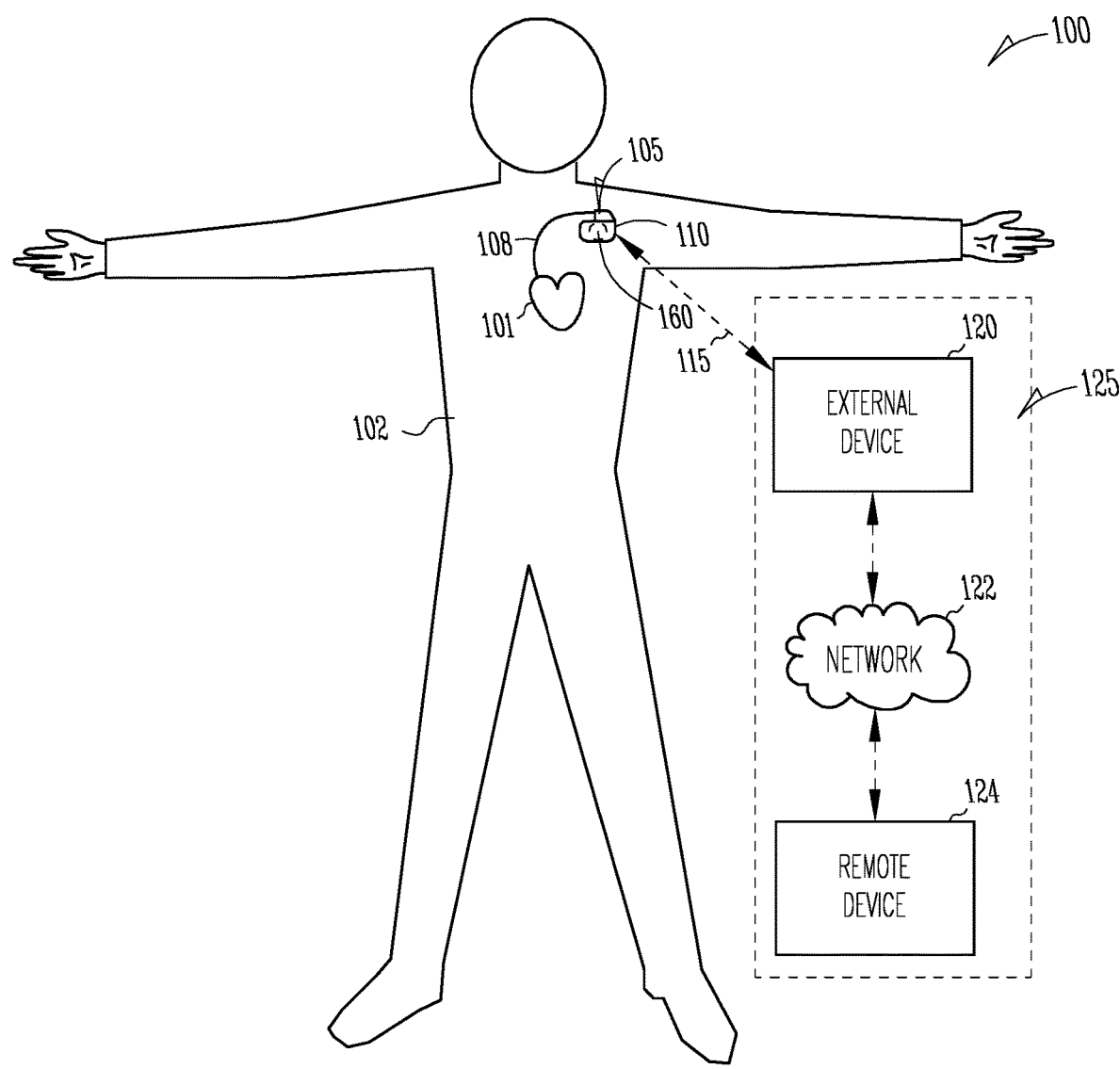
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities may be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AED)s) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

In an example, the AMD 110 may include a detector circuit 160 to detect a chronic medical condition, such as worsening heart failure (VHF), using the sensed physiological signals. In an example, the detector circuit 160 may analyze heart sounds (HS) data collected when the heart undergoes ventricular pacing and HS data collected when the heart is absent of ventricular pacing. Ventricular pacing may include epicardial or endocardial pacing of a ventricle, or pacing at a portion of the electrical conduction system of the heart such as the His bundle. The detector circuit 160 may determine a worsening heart failure indicator based on the paced HS metric and the sensed HS metric. In an example, the detector circuit 160 may determine a concordance indicator between a HS metric trend generated from the HS data corresponding to the paced ventricular contractions and a HS metric trend generated from the HS data corresponding to the intrinsic ventricular contractions. The concordance indicator may be used to identify causes of the detected WHF, such as due to reduced myocardial contractility or due to sub-optimal device programming (with preserved myocardial contractility). In an example, at least some of the HS analysis or concordance indicator determination may be implemented in and executed by the external system 125.

The AMD 110 may additionally include a therapy unit that may generate and deliver one or more therapies. The therapy may be delivered to the patient 102 via the lead system 108 and the associated electrodes. The therapies may include electrical, magnetic, or other types of therapy. Examples of the anti-arrhythmic therapy may include pacing, cardioversion, defibrillation, neuromodulation, drug therapies, or biological therapies, among other types of therapies. In an example, the therapy unit may be configured to deliver cardiac resynchronization therapy (CRT) or multisite pacing for rectifying dyssynchrony and improving cardiac function in CHF patients. In another example, the therapy unit may be configured to deliver anti-arrhythmic therapy to treat arrhythmias. In yet another example, the therapy unit may be a drug delivery system, such as a drug infusion pump, configured to deliver one or more medications to the patient to treat CHF, arrhythmias, or other medical conditions.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiological data, performing at least one self-diagnostic test (such as for a device operational status), analyzing the physiological data to detect a target medical condition such as WHF, or delivering or adjusting a therapy to the patient 102. Additionally, the external system 125 may receive device data from the AMD 110 via the communication link 115. Examples of the device data received by the external system 125 may include real-time or stored physiological data from the patient 102, diagnostic data such as detection of WHF events, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The external system 125, such as the external device 120 or the remote device 124, may output the detected medical events, such as an event of WHF, to a system user such as the patient or a clinician, or to a process including, for example, an instance of a computer program executable in a microprocessor. The process may include an automated generation of therapy and patient management recommendations. In an example, the AMD 110 may generate the HS metric trend corresponding to paced ventricular contractions and the HS metric trend corresponding to intrinsic ventricular contractions, and the external system 125 may generate the concordance indicator between the sensed and paced HS metric trends, and generate one or more of a therapy adjustment indicator and/or a worsening cardiac contractility indicator using the concordance indicator. The therapy adjustment indicator indicates the detected WHF is attributed to a reduction in the benefit of electrostimulation therapy under the present configuration and programming settings. Accordingly, an adjustment of electrostimulation therapy may be recommended to a clinician to rectify the WHF. The worsening cardiac contractility indicator indicates the detected WHF is attributed to pathological remodeling and degrading myocardial contractility. With reduced myocardial contractility, mere reprogramming of electrostimulation therapy may not achieve desired therapeutic benefits (such as enhanced cardiac synchrony and hemodynamics). A medical therapy, such as administration of inotropic agents, may be recommended to a clinician to bolster myocardial contractility, in lieu of or in addition to the electrostimulation therapy, to improve patient cardiac performance.

The external system 125 may include respective display units for displaying the physiological signals, or alerts, alarms, emergency calls, or other forms of warnings to signal the detection of WHF. The external system 125 may additionally display signal analysis results such as the concordance indicator, the therapy adjustment indicator and the worsening cardiac contractility indicator, or therapy and patient management recommendations, among other information.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
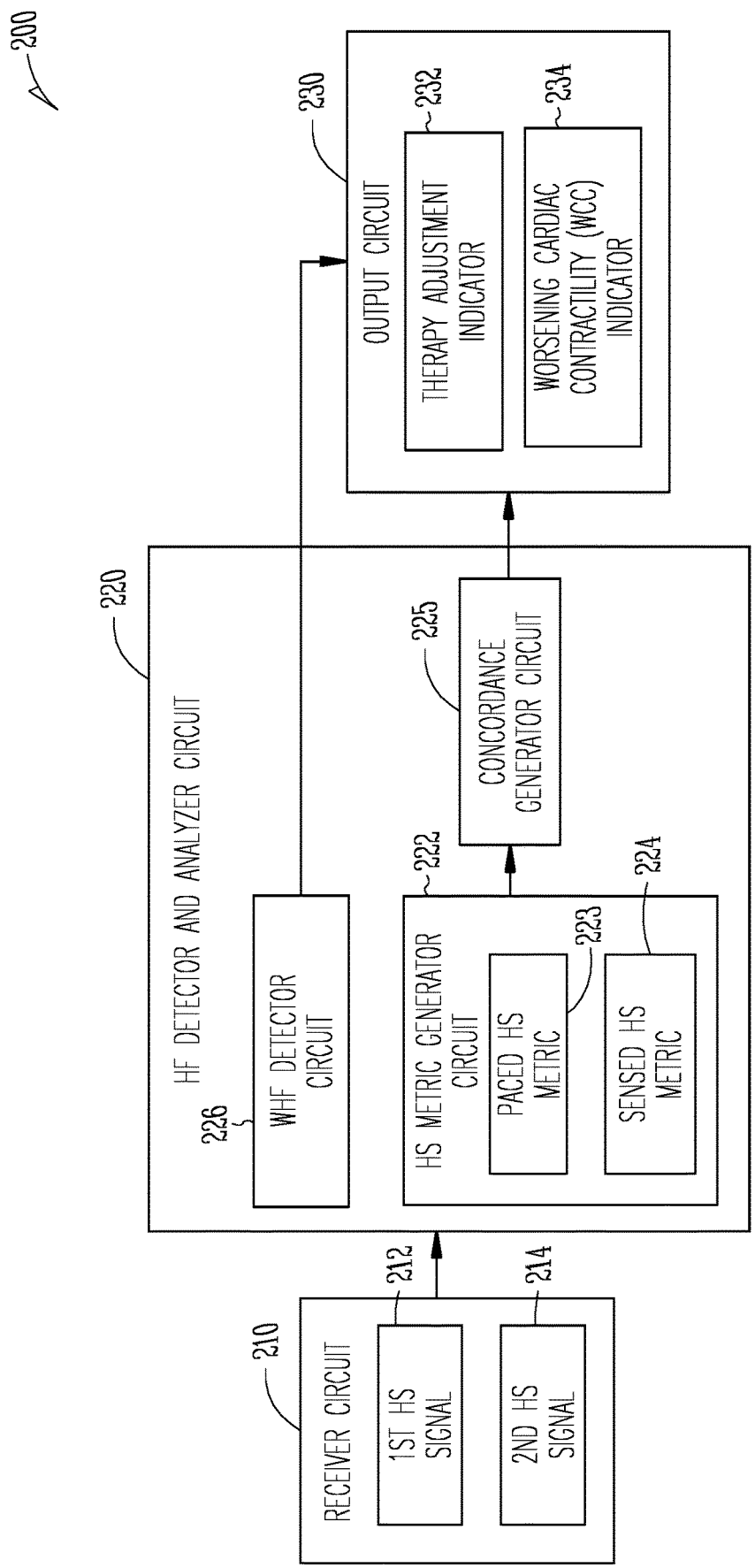
FIG. 2 illustrates generally an example of a medical event detection system configured to detect a medical event such as worsening heart failure (WHF).

FIG. 2 illustrates generally an example of a medical event detection system 200 configured to detect a medical event such as worsening heart failure (WHF), and to identify the causes of detected WHF. The medical event detection system 200 may include one or more of a receiver circuit 210, a detector and analyzer circuit 220, and an output circuit 230. Based at least in part on the identified causes of WHF the medical event detection system 200 may generate patient management recommendations, such as programming the electrostimulation therapy or administering HF drugs such as inotropic agents to bolster myocardial contractility.

At least a portion of the medical event detection system 200 may be implemented in the AMD 110, the external system 125 such as one or more of the external device 120 or the remote device 124, or distributed between the AMD 110 and the external system 125. In an example, the receiver circuit 210 and the HF detector and analyzer circuit 220 may be implemented in an AMD, and at least a portion of the output circuit 230 may be implemented in the external system 125, such as in a programmer or a remote patient management system. The external system 125 may generate the therapy adjustment indicator 232 and the worsening cardiac contractility indicator 234, and present the indicators to a user such as a clinician. A clinician may administer medical therapy, or program the AMD 110 via the communication link 115 with the desired parameter values. The AMD 110 may detect future WHF events using the programmed detection parameters, and deliver HF therapy in response to the detected WHF events.

The receiver circuit 210 may receive one or more physiological signals from a patient. In an example, the receiver circuit 210 may be coupled to a sensor circuit that includes a sense amplifier circuit to sense one or more physiological signals from a patient via one or more implantable, wearable, or otherwise ambulatory sensors or electrodes associated with the patient. The sensors may be incorporated into, or otherwise associated with an ambulatory device such as the AMD 110. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit may include one or more sub-circuits to digitize, filter, or perform other signal conditioning operations on the received physiological signal. In some examples, the physiological signals sensed from a patient may be stored in a data storage device, such as an electronic medical record (EMR) system. The receiver circuit 210 may receive a physiological signal from the data storage device in response to a data retrieval command from a system user.

In an example, the receiver circuit 210 may receive a first heart sounds (HS) signal 212 and a second HS signal 214. The receiver circuit 210 may be coupled to one or more HS sensors to sense HS signals. The first HS signal 212 may be collected during ventricular pacing, and the second HS signal 214 may be collected in during intrinsic ventricular contractions. The first HS signal 212 represents induced cardiac acoustic or mechanical activity in response to paced ventricular contractions, and the second HS signal 214 represents intrinsic cardiac acoustic or mechanical activity in response to intrinsic ventricular contractions. The ventricular pacing may be delivered following a latency period with respect to a fiducial point, such as a P wave sensed from an ECG or an intracardiac EGM. In another example, the ventricular pacing may be delivered following a latency period with respect to an atrial pacing. The first HS signal 212 and the second HS signal 214 may each be collected in the presence or in the absence of atrial pacing.

The ventricular pacing, during which the first HS signal 212 is collected, may be a part of the electrostimulation therapy such as CRT that involves pacing at one or both of the ventricles, multi site pacing therapy that involves pacing at two or more stimulation sites of the same heart chamber (e.g., the left ventricle) within a cardiac cycle, or His bundle pacing that involves pacing at a portion of the cardiac electrical conduction system. The electrostimulation therapy may be delivered via the AMD 110 or an external stimulator system. The first HS signal 212 may be acquired when the patient receives CRT, multisite pacing, or other electrostimulation therapy involving ventricular pacing, and the second HS signal 214 may be acquired when no ventricular pacing is activated and the patient is under intrinsic ventricular contractions. Alternatively, the ventricular pacing may be a part of a testing procedure, which may not be a part of the prescribed electrostimulation therapy regimen. The testing procedure is used to evaluate patient responses (such as heart sounds) under various cardiac stimulation challenges. In an example, the testing procedure may include one or more of temporary suspension of ventricular pacing during which the second HS signal 214 is collected, or temporary delivery of ventricular pacing during which the first HS signal 212 is collected.

The HF detector and analyzer circuit 220 may be configured to detect WHF and generate an indication of possible causes of WHF using the first and second HS signals 212 and 214. In an example, the HF detector and analyzer circuit 220 can be implemented as a part of a microprocessor circuit in the patient management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute a set of instructions of performing the functions, methods, or techniques described herein.

In an example such as illustrated in FIG. 2, the HF detector and analyzer circuit 220 may include circuit sets comprising one or more of a HS metric generator circuit 222, a concordance generator circuit 225, and a WHF detector circuit 226. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The HS metric generator circuit 222 may be configured to generate a paced HS metric 223 from the first HS signal, and a sensed HS metric 224 from the second HS signal. The paced HS metric 223 indicates cardiac contractility in the presence of ventricular pacing, and the sensed HS metric 224 indicates cardiac contractility during intrinsic ventricular contractions. The HS metric generator circuit 222 may detect from the first and second HS signals respective heart sound components, such as S1, S2, S3, or S4, and generate the paced HS metric 223 and the sensed HS metric 224 using the detected HS components. The HS components may be detected within respective HS detection windows. The HS detection windows may be determined with reference to a physiologic event such as R wave, Q wave, or QRS complexes obtained from an ECG or an intracardiac EGM synchronously sensed with the HS signal. In an example, a S1 detection window may begin at 50 milliseconds (msec) following a detected R wave of an ECG signal and have a duration of 300 msec. An S2 detection window can begin at specified offset following a detected R wave or S1 heart sound. An S3 detection window can be determined using at least one cardiac signal feature such as the R-wave timing or the timing of S2 heart sound. The S3 detection window can have a specified duration and can begin at a specified offset following the detected S2. In an example, the offset can be 125 msec, and the S3 window duration can be 125 msec. The offset or the S3 window duration can be a function of a physiologic variable such as a heart rate. In an example, the HS metric generator circuit 222 may calculate HS signal energy within the corresponding HS detection window, and detect the HS component in response to the calculated HS signal energy exceeding a specified threshold. In another example, the HS metric generator circuit 222 can detect the HS component adaptively by tracking the temporal locations of the previously detected HS component. A dynamic programming algorithm can be used to detect and track heart sound components, such as that disclosed in the commonly assigned Patangay et al. U.S. Pat. No. 7,853,327 entitled "HEART SOUND TRACKING SYSTEM AND METHOD," which is hereby incorporated by reference in its entirety.

The paced HS metric 223 and the sensed HS metric 224 may include temporal, statistical, or morphological features of one or more HS components detected respectively from the first and second HS signals. In an example, the paced HS metric 223 may include a paced S1 intensity ($\|pS1\|$) indicating cardiac contractility during ventricular pacing, and the sensed HS metric 224 includes a sensed S1 intensity ($\|sS1\|$) indicating cardiac contractility during intrinsic ventricular contractions and absent of ventricular pacing. Examples of the intensity of HS component may include amplitude of a detected HS component in a time-domain HS signal, a transformed HS signal such as integrated HS energy signal, or in a frequency-domain HS signal, such as the peak value of the power spectral density, or peak value of a generic measurement within the respective HS detection window, such as peak envelop signal or root-mean-squared value of the portion of the HS signal within the HS detection window. The intensity of a HS component can also include a rate of change of signal amplitude or peak energy. In an example, the HS metrics can include an intensity measure of a portion of the HS signal that includes at least a portion of a specified HS component, such as a root-mean-squared value of the HS signal portion between an R wave and a subsequent S1 heart sound, or between an R wave and a subsequent S2 heart sound, within the same cardiac cycle.

Alternatively or additionally, the HS metric generator circuit 222 may generate the paced HS metric 223 and the sensed HS metric 224 each representing the electromechanical coupling of the heart, such as a paced cardiac timing interval (pCTI) using the first HS signal, or a sensed. CTI (sCTI) using the second HS signal. The cardiac timing interval (CTI) may be measured between a cardiac electrical event such as detected from the cardiac electrical signal and a mechanical event such as detected from the HS signal. The CTI may include a pre-ejection period (PEP), a systolic timing interval (STI), or a diastolic timing interval (DTI), among others. The PEP represents the total duration of the electrical and mechanical events prior to ejection, and can be measured as the time duration from the onset of the QRS to the S1 heart sound, that is, PEP≈Q-S1 interval. Alternatively, the PEP can be measured from the ventricular pacing (Vp) signal to the beginning of ventricular ejection such as represented by the onset of S1 heart sound, that is, PEP≈Vp-S1 interval. The STI represents the duration of total electro-mechanical systole, and contains two major components, namely the PEP and the LVET. The STI can be measured as an interval from the onset of the QRS complex on the ECG or the atrial activation event in an intracardiac EGM to the S2 heart sound, that is, STI≈Q-S2 interval. In the case when the ventricle is paced (Vp), the STI can be measured from the ventricular pacing (Vp) signal to the end of ventricular ejection such as represented by the onset of S2 heart sound, that is, STI≈p-S2 interval. The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle, that is, DTI≈S2-Q interval. In some examples, the HS metric generator circuit 222 may generate composite measures such as PEP/LVET ratio, STI/DTI ratio, STI/cycle length (CL) ratio, or DTI/CL ratio, among others.

The concordance generator circuit 225 may be coupled to the HS metric generator circuit 222, and configured to determine a concordance indicator between the paced HS metric 223 and the sensed HS metric 224. The concordance indicator may represent a temporal pattern of covariation between the paced and the sensed HS metrics. In an example, the concordance generator circuit 225 may respectively trend the paced HS metric 223 and the sensed HS metric 224 over multiple cardiac cycles or over a period of time. The resulting paced HS metric trend (e.g., ||pS1|| trend or pCTI trend) or the sensed HS metric trend (e.g., ||sS1|| trend or sCTI trend), may represent a growth trend indicating an increase of the corresponding HS metric over time, a decay trend indicating a decrease of the corresponding HS metric over time, or a flat trend indicating no substantial change in the corresponding HS metric over time. The HS metric trend may be quantified using a slope of trend. A positive slope represents a growth trend, and a negative slope represents a decay trend.

The HS metric trend may be affected by confounding factors such as heart rate or timing of ventricular contractions(intrinsic or paced) with respect to the atrial contractions. For example, heart rate may affect myocardial contractility and S1 intensity, as both are driven by common sympathetic innervation. The myocardial contractility and the electromechanical coupling of the heart (e.g., CTI) may be affected by an atrioventricular delay (AVD) that determines the timing of the ventricular pacing. To mitigate the impact of the confounding factors on the HS metric trend, the concordance generator circuit 225 may trend the paced and the sensed HS metrics over multiple cardiac cycles having substantially similar cycle lengths or heart rates within a specified tolerance, such as approximately 100±5 beats per minute (bpm) in a non-limiting example. In another example, the concordance generator circuit 225 may trend the paced HS metric 223 and the sensed HS metric 224 under substantially similar AVD, such as approximately 180 msec, in a non-limiting example.

The concordance generator circuit 225 may determine the concordance indicator using the paced HS metric trend relative to the sensed HS metric trend. The concordance indicator may include a qualitative descriptor of the paced ITS metric trend and the sensed HS metric trend, such as a decay trend of ||pS1|| together with a flat trend of ||sS1|| or a negative slope of ||pS1|| trend exceeding a slope threshold together with a slope of ||sS1|| trend within a slope range. Alternatively, the concordance indicator may include a quantitative measure. In an example, the concordance indicator includes a correlation between the paced HS metric trend and the sensed HS metric trend, such as a correlation between the ||pS1|| trend and the ||sS1|| trend, or a correlation between the pCTI trend and the sCTI trend. A positive correlation indicates similar trends between the paced and the sensed HS metric trends (e.g., both are growth trends). A negative correlation indicates opposite trends between the paced the sensed HS metric trends (e.g., the paced HS metric trend is a decay trend, while the sensed. HS metric trend is a growth trend). In another example, the concordance indicator may be determined using a ratio of a temporal change of the sensed HS metric to a temporal change of the paced HS metric, such as a ratio of a change in sensed S1 intensity (Δ||sS1||) to a change in paced S1 intensity (Δ||pS1||), or a ratio of a change in sensed CTI (ΔsCTI) to a change in paced CTI (ΔpCTI).

The WHF detector circuit 226 may detect a worsening heart failure (WHF) event using the physiological information received from the receiver circuit 210. The WHF detector circuit 226 may generate a signal metric from a physiological signal, compare the signal metric to an onset threshold to detect an onset of WHF event, or compare the signal metric to a reset threshold to detect a termination of WHF event. In an example, the WHF detector circuit 226 may use one or more HS metrics from the HS metric generator circuit 222 to detected WHF. For example, the WHF detector circuit 226 may detect WHF if S3 intensity ||S3||, such as S3 amplitude or signal energy within the S3 detection window, exceeds an onset threshold. A louder S3 such as the ||S3|| exceeding an S3 intensity threshold indicates reduced ventricular compliance and deteriorating diastolic function, signifying occurrence of WHF. Additionally or alternatively, the WHF detector circuit 226 may use sensed or paced S1 intensity or CTI measurements, such as generated by the HS metric generator circuit 222, to detect WHF. For example, the WHF detector circuit 226 may detect WHF if a decay trend of the paced S1 intensity, or a decay trend of paced CTI, falls below their respective thresholds, indicating poor cardiac contractility or reduced electromechanical coupling that signifies occurrence of WHF.

In some examples, the WHF detector circuit 226 may generate a composite signal index using a combination of signal metrics derived from the one or more physiological signals. Examples of the signal metrics may include heart rate, heart rate variability, respiratory rate, rapid-shallow breathing index, one or more heart sounds S1, S2, S3 or S4, a ratio of one HS component to another HS component, thoracic impedance, physical activity or exertion level, among others. The WHF detector circuit 226 may trend the composite signal index over time, and detect WHF and generate a WHF alert when the composite signal index exceeds a threshold.

In some examples, the WHF detector circuit 226 may process the signal metric trend and generate a predictor trend indicating temporal changes of the signal metric trend. The temporal change may be calculated using a difference between short-term values and baseline values. In an example, the short-term values may include statistical values such as a central tendency of the measurements of the signal metric within a short-term window of a first plurality of days. The baseline values may include statistical values such as a central tendency of the measurements of the signal metric within a long-term window of a second plurality of days preceding the short-term window in time. In some examples, the predictor trend may be determined using a linear or nonlinear combination of the relative differences between multiple short-term values corresponding to multiple first time windows and multiple baseline values corresponding to multiple second time windows, wherein the differences may be scaled by respective weight factors which may be based on timing information associated with corresponding multiple short-term window, such as described by Thakur et al., in U.S. Patent Publication 2017/0095160, entitled "PREDICTIONS OF WORSENING HEART FAILURE", which is herein incorporated by reference in its entirety.

The output circuit 230, coupled to the WHF detector circuit 226 and the concordance generator circuit 225, may be configured to generate one or more of a therapy adjustment indicator 232 or a worsening cardiac contractility (WCC) indicator 234, in response to the detected WHF event. The therapy adjustment indicator 232 indicates that the detected WHF is attributed to a reduction in the benefit of electrostimulation therapy (e.g., CRT, multisite pacing, His bundle pacing, or neurostimulation) under the present configuration and programming settings, and that the patient has preserved myocardial contractility. Accordingly, further adjustment of electrostimulation therapy may provide additional benefit in rectifying WHF. The WCC indicator 234 indicates that the detected WHF is attributed to pathological remodeling and degrading myocardial contractility. As a result, mere reprogramming of pacing therapy may not achieve desired therapeutic benefits. Instead, medical therapies such as inotropic agents may be administered, in lieu of or in addition to electrostimulation therapy, to bolster myocardial contractility.

The output circuit 230 may generate the therapy adjustment indicator 232 when the concordance indicator satisfies a first condition, and generate the WCC indicator 234 when the concordance indicator satisfies a different second condition. In an example, the concordance indicator is qualitatively represented by the trends or the slopes of trends of the sensed and paced HS metrics. The output circuit 230 may generate the therapy adjustment indicator 232 when there is a decay trend of ||pS1|| together with a flat trend of ||sS1||. The output circuit 230 may generate the WCC indicator 234 when both ||pS1|| and ||sS1|| manifest decay trends. In an example, the concordance indicator is quantitatively represented by a correlation between the paced HS metric trend and the sensed HS metric trend, such as a correlation between ||pS1|| trend to ||sS1|| trend, or between ΔpCTI trend and ΔsCTI trend. The output circuit 230 may generate the therapy adjustment indicator 232 when the correlation falls below a threshold indicating lack of concordance between the paced HS metric 233 and the sensed HS metric 234, and generate the WCC indicator 234 when the correlation exceeds a threshold or falls within a range indicating that both the paced and the sensed HS metrics decrease over time. In another example, the concordance indicator is measured using a HS ratio of a temporal change of the sensed HS metric 224 to a temporal change of the paced HS metric 223, such as an S1 intensity ratio Δ||sS1||/Δ||pS1||, or a CTI ratio ΔsCTI/ΔpCTI. The output circuit 230 may generate the therapy adjustment indicator 232 when the HS ratio falls below a positive threshold value, and generate the WCC indicator 234 when the HS ratio exceeds a threshold indicating higher degree of concordance between the paced and the sensed HS metrics. Examples of the concordance indicator between the sensed and paced HS metric and the therapy adjustment indicator 232 and the WCC indicator 234 are discussed below, such as with reference to FIG. 4-B.

In some examples, the HS metric generator circuit 222 may classify the paced HS metric 223 into a first paced HS metric corresponding to paced atrial contractions and a second paced HS metric corresponding to intrinsic atrial contractions (i.e., absent of atrial pacing). The first paced HS metric is generated using a portion of the first HS signal when both atrium and ventricle are paced, where the ventricular pacing is delivered at a paced AVD (pAVD) with respect to an atrial pacing pulse within the same cardiac cycle. The second paced HS metric is generated using a different portion of the first HS signal when the atrium is not paced, where the ventricular pacing is delivered at a sensed AVD (sAVD) with respect to an intrinsic atrial activation (e.g., P wave in an ECG or an intrinsic atrial activation sensed in an EGM) within the same cardiac cycle. The concordance generator circuit 225 may determine a first concordance indicator between the first paced HS metric and the sensed HS metric, such as a correlation or a ratio between ||pS1|| corresponding to atrial pacing and ||sS1||; and a second concordance indicator between the second paced HS metric and the sensed HS metric, such as a correlation or a ratio between ||pS1|| corresponding to intrinsic atrial activation and ||sS1||. The output circuit 230 may generate the therapy adjustment indicator 232 including recommendations to respectively adjust the pAVD according to the first concordance indicator, or adjust the sAVD according to the second concordance indicator.

The output circuit 230 may additionally include circuitry configured to generate a human-perceptible notification of the detected WHF event. The output circuit 230 may be coupled to a display for displaying the received physiological information such as the first and second HS signals 212 and 214, the paced and the sensed HS metrics 223 and 224, the concordance indicator, the therapy adjustment indicator 232 and a recommendation for adjustment of electrostimulation therapy, the WCC indicator 234 and a recommendation to administer medical therapies such as inotropic agents, among other intermediate measurements or computations. In an example, the output circuit 230 may generate and display trends of the paced and the sensed HS metrics 223 and 224, or trends of HS intensity ratio or CTI ratio. In an example, the trends include daily trends comprising representative daily values of the paced and the sensed HS metrics 223 and 224, or representative daily HS intensity ratios or the CTI ratios. The output circuit 230 may be coupled to a printer for printing hard copies of the HF detection and analysis information. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected WHF event.

The output circuit 230 may be included in a user interface. In an example, at least a portion of the user interface may be implemented in the external system 125. The user interface may include an input unit that may receive user input that controls the WHF detection or concordance indicator generation, and receive user confirmation, rejection, or otherwise modification of the recommendations of programing of electrostimulation therapy or administration of medical therapy. The input unit may include an input device such as a keyboard, on-screen keyboard, mouse, trackball, touchpad, touch-screen, or other pointing or navigating devices.

Figure 3:
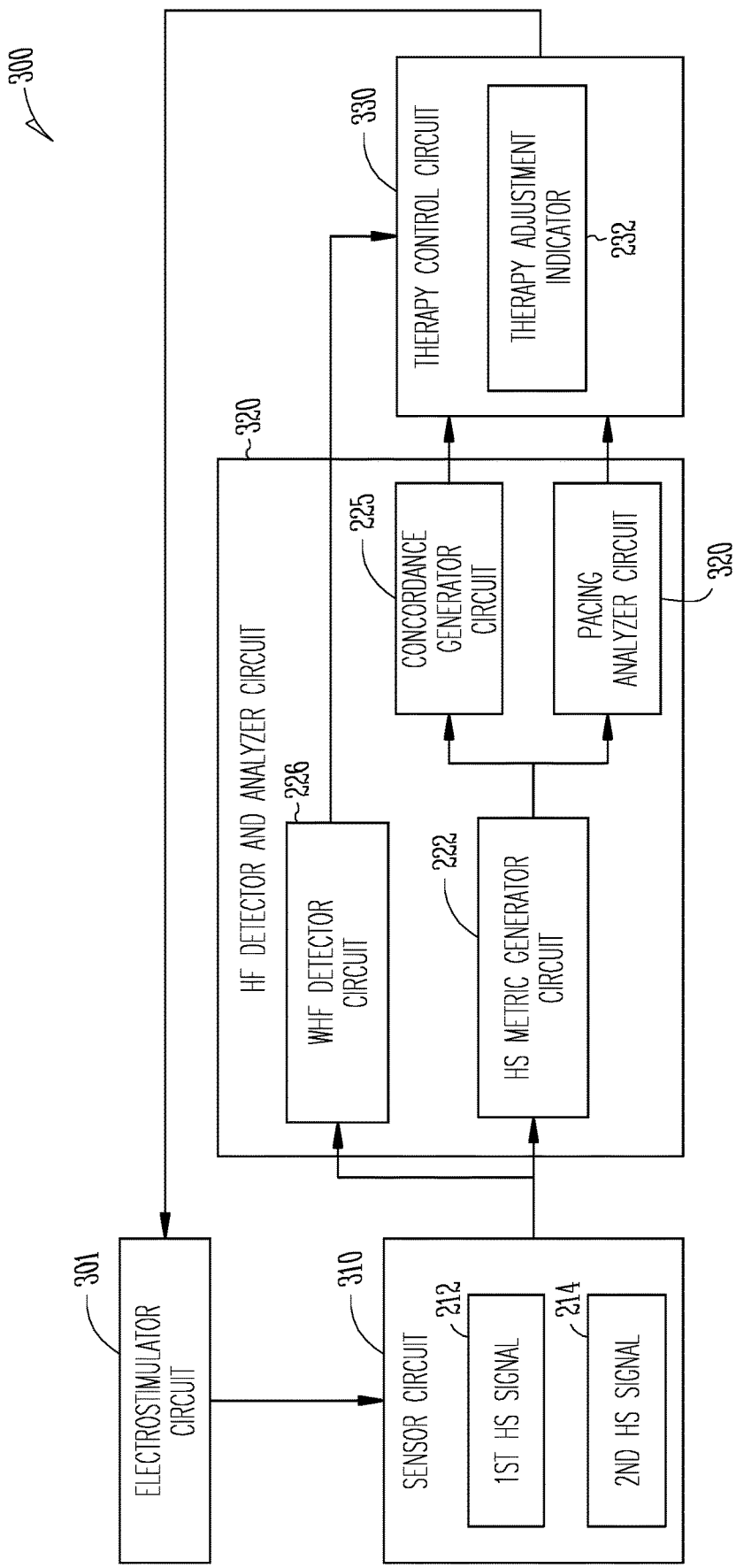
FIG. 3 illustrates generally an example of a feedback-controlled heart failure management system 300 configured to provide electrostimulation therapy.

FIG. 3 illustrates generally an example of a feedback-controlled heart failure management system 300 configured to provide electrostimulation therapy. The electrostimulation therapy may be initiated or adjusted based on an identification of the causes of the detected WHF event. The system 300 is an embodiment of the medical event detection system 200. As illustrated in FIG. 3, the system 300 may include an electrostimulator circuit 301, a sensor circuit 310, a HF detector and analyzer circuit 320, and a therapy control circuit 330.

The electrostimulator circuit 301 may be configured to generate electrostimulation in response to a WHF event. Examples of the electrostimulation may include cardiac pacing therapy, cardioversion therapy, defibrillation therapy, or other stimulation therapies using a specified energy source. Alternatively or additionally, electrostimulation may be applied to non-cardiac tissues such as nerve tissues, muscle tissues, among other excitable tissues of the patient.

The electrostimulator circuit 301 may generate electrostimulation according to programmed therapy control parameters, such as provided by the therapy control circuit 330. Examples of the therapy control parameters may include stimulation site, stimulation mode, or timing and strength of stimulation, among other parameters. Electrostimulation may be delivered to the pacing sites via one or more leads of the lead system 108 and the respectively attached electrodes. The stimulation mode may include cardiac resynchronization therapy (CRT), which may be a biventricular (BiV) pacing of both left and right ventricles, or synchronized left ventricle (LV)-only pacing. The stimulation mode may also include single site pacing of only one site of a heart chamber (e.g., the left ventricle) within a cardiac cycle, or multisite pacing (MSP) of two or more sites of a heart chamber within the same cardiac cycle. In an example, the MSP may be delivered within the LV. Two or more LV sites may be selected for pacing via multiple LV electrodes. The LV MSP may have a unipolar pacing configuration involving only one LV electrode (e.g., as the cathode), a bipolar pacing configuration involving two LV electrodes (e.g., as the cathode and anode), or a tripolar configuration involving two LV electrodes used jointly as the cathode, or two electrodes such as selected from the right atrium and the right ventricle electrodes used jointly as the anode. The stimulation mode may also include His bundle pacing at a portion of the cardiac electrical conduction system.

Stimulation strength parameters controls the amount of energy delivered to the pacing site. Examples of the stimulation strength parameters may include pulse width, pulse amplitude, frequency, duty cycle, or stimulation duration. Stimulation timing parameters determine the timing and sequence of electrostimulation pulses, and may have an impact on therapy efficacy and hemodynamic outcome. During CRT, synchronized stimulation may be applied to the LV and the RV of a heart. The RV and LV pacing sites may be stimulated simultaneously, or sequentially with an RV-LV interventricular pacing delay (VVD). Delivery of LV and RV pacing may be timed relative to a fiducial point, such as an intrinsic atrial depolarization sensed by an atrial electrode (atrial sense, or AS), or an atrial pacing pulse (AP) that elicits atrial activation. If no intrinsic ventricular depolarization is detected within a period of atrial-ventricular delay (AVD) following the AS or the AP, the LV and RV pacing may be delivered at the end of the AVD. In MSP such as at the left ventricle, multiple LV sites may be simultaneously stimulated, or separated by one or more intra-LV time offset.

The sensor circuit 310 may be coupled to one or more HS sensors configured to sense acoustic or mechanical vibration of a heart. The HS sensor may be an implantable, wearable, or otherwise ambulatory sensor, and placed external to the patient or implanted inside the body. The HS sensors may be included in an implantable system, such as an implantable medical device, or a lead coupled to the implantable medical device. Various sensor types may be used to sense the HS signal. In an example, the HS sensor is an accelerometer configured to sense an acceleration signal indicative of the heart sound of the subject. In another example, the HS sensor is an acoustic sensor configured to sense an acoustic energy indicative of the heart sound of the subject. Other sensors, such as microphone, piezo-based sensor, or other vibrational or acoustic sensors may also be used to sense the HS signal.

The sensor circuit 310 includes a sense amplifier circuit to pre-process the sensed HS signal. The pre-processing can include amplification, digitization, filtering, or other signal conditioning operations. In an example, the receiver circuit 210 may include a bandpass filter adapted to filter the received HS signal to a frequency range of approximately between 5 and 90 Hz. In another example, the signal conditioning circuit may include a bandpass filter adapted to filter the received HS signal to a frequency range of approximately between 9 and 90 Hz. In an example, the sensor circuit 310 may include a double or higher-order differentiator configured to calculate a double or higher-order differentiation of the received HS signal.

The sensor circuit 310 may sense the first HS signal 212 when the electrostimulator circuit 301 delivers ventricular pacing, and sense the second HS signal 214 when the electrostimulator circuit 301 withholds ventricular pacing. The ventricular pacing may be part of the CRT, single site pacing, multisite pacing, or His bundle pacing provided by the electrostimulator circuit 301. In an example, the electrostimulation circuit 301 may execute a testing procedure including a first testing phase of delivering ventricular pacing at specified heart rate, AVD, or other pacing parameters under a controlled condition, and a second testing phase of suspending the ventricular pacing at least temporarily for a specified time period. The sensor circuit may sense the first HS signal during the first phase, and sense the second HS signal during the second testing phase. In another example, the HS signal acquisition and analysis in the presence or in the absence of ventricular pacing may be triggered by certain events, such as after device reprogramming, lead repositioning, clinical intervention, a substantial change in a signal metric or a composite signal metric indicative of WHF, or an indication of electrical remodeling or reverse remodeling such as indicated by a substantial change in RV-LV timing, among others. The event-triggered HS assessment and concordance analysis requires no interruption (e.g., temporary suspension) of an ongoing therapy, and thus may be beneficial for patients requiring sustained pacing therapy.

The HF detector and analyzer circuit 320, which is an embodiment of the HF detector and analyzer circuit 220, may include a HS metric generator circuit 222 that may generate HS metrics, including the paced HS metric 223 and the sensed HS metric 224. The concordance generator circuit 225 may generate a concordance indicator, which may include a qualitative descriptor or a quantitative measure of the temporal covariation pattern between the paced HS metric 223 and the sensed HS metric 224, as discussed with reference to FIG. 2. The HF detector and analyzer circuit 320 may additionally include a pacing analyzer circuit 320 configured to produce a pacing effectiveness indicator using the paced and the sensed HS metrics, such as a CRT therapy effectiveness indicator. In an example, the pacing effectiveness indicator is determined using the paced S1 intensity ($\|pS1\|$) relative to the sensed S1 intensity ($\|sS1\|$), such as an intensity ratio $\|pS1\|/\|sS1\|$. An effective ventricular pacing may produce a stronger S1 than the sensed S1 corresponding to intrinsic ventricular contractions, resulting in a larger intensity ratio $\|pS1\|/\|sS1\|$. The pacing analyzer circuit 320 may compare the intensity ratio $\|S1\|/\|sS1\|$ to a threshold (TH) to quantify the effectiveness of pacing. The threshold may be determined using a baseline $\|pS1\|/\|sS1\|$ ratio ($R_0$) such as determined under a controlled condition of heart rate, AVD, or other pacing parameters. In an example, the threshold TH may be determined as the larger of $0.7*R_0$ and one, that is, TH=max ($0.7*R_0$, 1). If the intensity ratio $\|pS1\|/\|sS1\|$ is less than threshold TH, then an indication of ineffective pacing may be used for generating the therapy adjustment indicator 232.

The pacing analyzer circuit 320 may determine a capture status using the HS metrics provided by the HS metric generator circuit 222. Response to electrostimulation such as CRT may be characterized by how frequent the delivered stimulation may capture the viable tissue by eliciting a propagatable cardiac depolarization. A capture occurs when a pacing pulse evokes a positive cardiac tissue response. A non-capture occurs when a pacing pulse fails to evoke a positive cardiac tissue response. A fusion occurs when a pacing pulse is delivered coincidental to a depolarization by an intrinsic cardiac activation. In an example, the pacing analyzer circuit 320 may determine capture status using a measure of electromechanical coupling, such as an interval from the P wave on an ECG or an atrial pacing pulse, to S2 within a cardiac cycle. If such P–S2 interval is shorter than a threshold, or increases by a specific percentage over time, a loss of capture is indicated. The capture status may be used for generating the therapy adjustment indicator 232.

The therapy control circuit 330, coupled to the HF detector and analyzer circuit 320, may be configured to identify the causes of the WHF event detected by the WHF detector circuit 226. If the concordance indicator indicates a lack of concordance between the sensed and paced HS metrics, the therapy control circuit 330 may determine that the WHF is attributed to a reduction in the benefit of electrostimulation therapy under the present configuration and programming settings. In response to the detected WHF, the therapy control circuit 330 may generate a therapy adjustment indicator 232 using one or more of the concordance indicator, the pacing effectiveness indicator, or the capture status. The therapy adjustment indicator 232 may include a recommendation for programing the electrostimulation therapy, such as adjusting one or more of stimulation mode, stimulation site, or parameters controlling stimulation timing or stimulation strength. For example, if the concordance indicator indicates a lack of concordance, or if intensity ratio $\|pS1\|/\|sS1\|$ falls below the threshold indicating reduced pacing effectiveness, or if loss of capture is indicated for ventricular pacing, or a combination of two or more of these conditions are satisfied, then the electrostimulator circuit 301 may be reprogrammed. Examples of the reprogramming may include: activating electrostimulation at more pacing sites; changing the pacing mode to BiV or multisize pacing; switching to different pacing sites with late activation; adjusting one or more timing parameters including AVD (e.g., lengthening AVD to improve ventricular filling) or a left ventricular-right ventricular delay (VVD); adjusting a lower rate limit (LRL) that represents a lowest rate that a cardiac stimulation may be initiated (e.g., increasing the LRL to promote atrial pacing, or decreasing the LRL to promote atrial sensing); adjusting sensor-indicated rate responsive pacing such as turning on the rate responsive pacing to promote atrial pacing at higher rates, or turning off rate responsive pacing to promote atrial sensing at higher rates; adjusting rate threshold for detecting atrial or ventricular tachyarrhythmias; or increasing pacing amplitude or stimulation duration; among other programming changes. In some examples, the therapy control circuit 330 may generate the worsening cardiac contractility (WCC) indicator 234 when the concordance indicator indicates a higher concordance between the paced and the sensed HS metrics, such as both $\|pS1\|$ and $\|sS1\|$ demonstrate decay trends. The therapy control circuit 330 may control a drug delivery system, such as a drug infusion pump, to deliver medications such as inotropic agents to the patient automatically or optionally with clinician intervention, as discussed with reference to FIG. 2. Alternatively or additionally, the therapy control circuit 330 may control an autonomic modulation therapy system to deliver neuromodulation therapy such as vagal nerve stimulation to improve cardiac contractility.

FIGS. 4A-B illustrate examples of S1 amplitude trends in the presence or absence of ventricular pacing when patient HF status worsens. The illustrated S1 amplitude trends may be generated using the HS metric generator circuit 222. FIG. 4A illustrates a paced S1 amplitude ($\|pS1\|$) series 411, and a sensed S1 amplitude ($\|sS1\|$) series 412. The $\|pS1\|$ series 411 is generated using multiple S1 measurements from a heart sound signal during ventricular pacing under a controlled condition such as the heart rates or the AVD within their respective ranges. The $\|sS1\|$ series 412 is generated using multiple S1 measurements from a heart sound signal in the absence of ventricular pacing, such as by temporarily withholding ventricular pacing during a testing procedure. As the HF status worsens, $\|pS1\|$ series decreases over time, corresponding to a decay trend 413; however, $\|sS1\|$ series does not decrease but instead maintains at a level over time, corresponding to a flat trend 414. No substantial change in S1 intensity signifies persevered myocardial contractility. Using the difference between the decay trend 413 of $\|PS1\|$ and the flat trend 414 of $\|sS1\|$ the concordance generator circuit 225 may generate a concordance indicator indicating that the WHF is attributed to reduced benefit of electrostimulation therapy under the present configuration and programming settings. Accordingly, a therapy adjustment indicator may be generated to recommend adjustment of electrostimulation therapy.

FIG. 4B illustrates a paced S1 amplitude ($\|pS1\|$) series 421 and a sensed S1 amplitude ($\|sS1\|$) series 422. The $\|pS1\|$ series 421 is generated during ventricular pacing, and the $\|sS1\|$ series 422 is generated in the absence of ventricular pacing, such as during intrinsic ventricular contractions. In response to worsened heart failure status, the $\|pS1\|$ series 421 decreases over time, corresponding to a decay trend 423. The $\|sS1\|$ series 422 also decreases over time, corresponding to a decay trend 424. The decay trend 424 of the sensed S1 intensity signifies reduced myocardial contractility. The high concordance between the decay trend 423 of $\|pS1\|$ and the decay trend 424 of $\|sS1\|$ indicates that the WHF is attributed to pathological remodeling and degrading myocardial contractility. Accordingly, medical therapies such as inotropic agents may be recommended, in addition to or in lieu of electrostimulation therapy.

Figure 5:
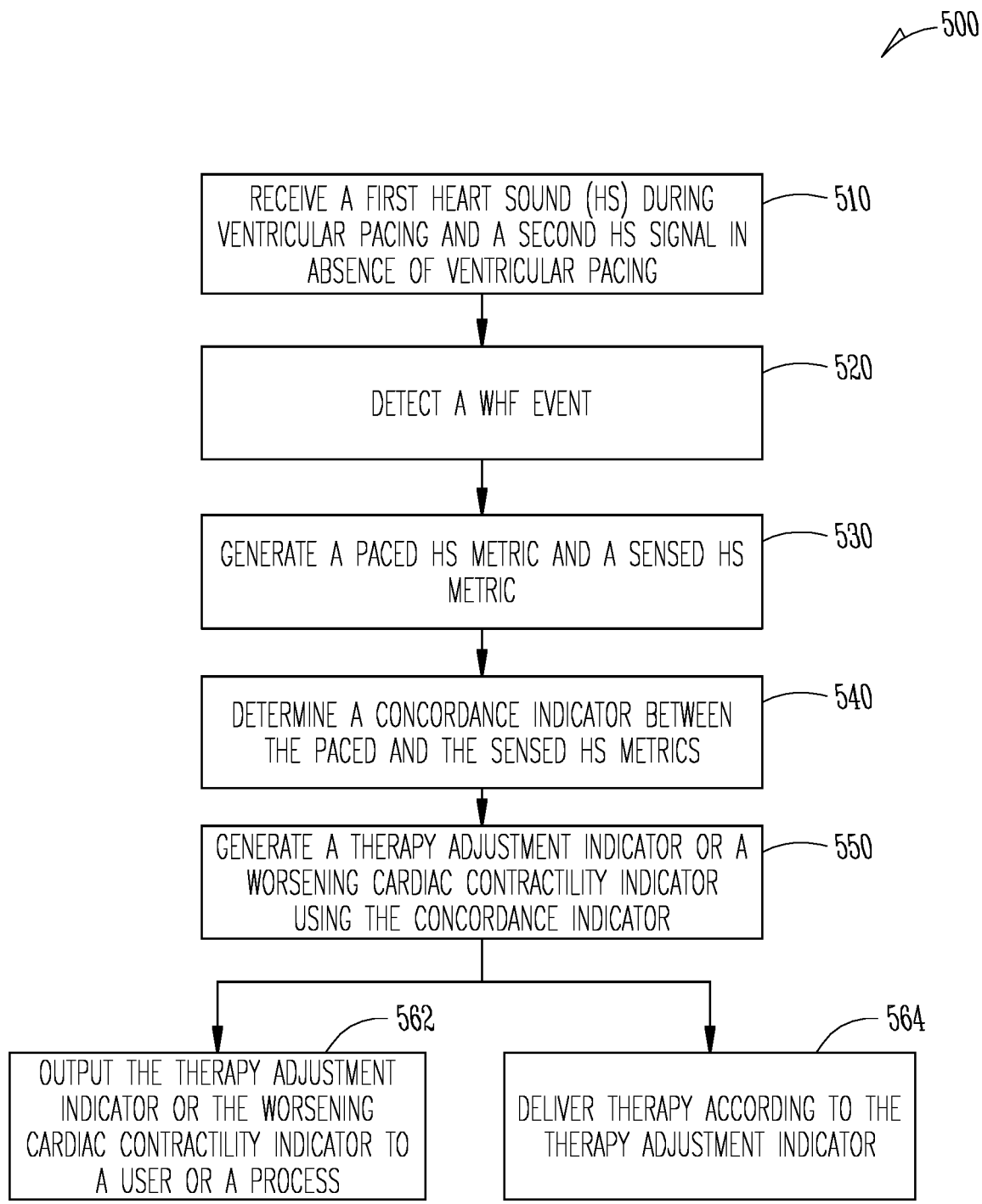
FIG. 5 illustrates generally an example of a method for adjusting a heart failure therapy.

FIG. 5 illustrates generally an example of a method 500 for adjusting a heart failure therapy. The method 500 may be implemented and executed in an ambulatory medical device such as an implantable or wearable medical device, or in a remote patient management system. In an example, the method 500 may be implemented in, and executed by, the AMU 110, one or more devices in the external system 125, or the medical event detection system 200 or the feedback-controlled heart failure management system 300.

The method 500 begins at 510, where physiological information may be received, such as via the receiver circuit 210. The physiological information may include one or more physiological signals sensed from a patient via one or more implantable, wearable, or otherwise ambulatory sensors or electrodes associated with the patient. In an example, the received physiological information may include a first HS signal collected during ventricular pacing, and a second HS signal collected during the intrinsic ventricular rhythm in the absence of ventricular pacing. The ventricular pacing, during which the first HS signal is collected, may be delivered at a specific latency period following an intrinsic atrial electrical activation or following an atrial pacing. The ventricular pacing may be a part of the electrostimulation therapy, such as a CRT or multisite pacing. Alternatively, the ventricular pacing may be a part of a testing procedure involving, for example, temporary suspension or delivery of ventricular pacing, to evaluate HS responses. The first and second HS signals may each be collected in the presence or in the absence of atrial pacing.

At 520, worsening heart failure (WHF) may be detected using the received physiological information, such as via the WHF detector circuit 226. In an example, the WHF may be detected using the first or the second HS signals. In an example, a VHF event may be detected if an amplitude or signal energy of a HS component (e.g., S3), exceeds a threshold. In an example, a composite signal index may be generated using a combination of signal metrics derived from the one or more physiological signal. A WHF event may be detected if the composite signal index exceeds a threshold. In some examples, a predictor trend indicating temporal changes of the signal metric trend may be calculated using a difference between short-term values and baseline values of a signal metric or a composite signal metric. The baseline values may include statistical values such as a central tendency of the measurements of the signal metric within a long-term window preceding a short-term window from which the short-term values are computed. A WHF event is detected if the predictor trend exceeds a threshold.

At 530, a paced HS metric may be generated from the first HS signal, and a sensed HS metric may be generated from the second HS signal. From the first and second HS signals, respective heart sound components, such as S1, S2, S3, or S4 heart sounds, may be detected. The HS components may be detected within respective HS detection windows. The paced HS metric and the sensed HS metric may include temporal, statistical, or morphological features of one or more HS components.

In an example, the paced HS metric includes a paced S1 intensity (∥pS1∥) indicating cardiac contractility in response to paced ventricular contractions, and the sensed HS metric includes a sensed S1 intensity (∥sS1∥) indicating cardiac contractility in the absence of ventricular pacing, such as during intrinsic ventricular rhythm. In another example, the paced HS metric and the sensed HS metric may include a measure of cardiac electromechanical coupling, such as cardiac timing interval (CTI) corresponding to paced ventricular contractions (pCTI) using the first HS signal, or a CTI corresponding to intrinsic ventricular contractions (sCTI) using the second HS signal. Examples of the CTI may include a pre-ejection period (PEP), a systolic timing interval (STI), or a diastolic timing interval (DTI), among others.

At 540, a concordance indicator between the paced HS metric and the sensed HS metric may be determined, such as via the concordance generator circuit 225. The concordance indicator may represent a temporal pattern of covariation between the paced and the sensed HS metrics. In an example, a trend of paced HS metric and a trend of sensed HS metric may be generated over multiple cardiac cycles or over a period of time. A growth trend indicates a temporal increase of the corresponding HS metric, a decay trend indicates a temporal decrease of the corresponding HS metric, or a flat trend indicates no substantial change in the corresponding HS metric over time. To reduce the impact of fluctuations of heart rate or different ventricular activation timings (e.g., AVD), the paced HS metric trend or the sensed HS metric trend may be generated under respectively controlled conditions, such as at substantially similar heart rates or substantially similar AVDs.

In an example, the concordance indicator may be generated using the paced HS metric trend relative to the sensed HS metric trend. The concordance indicator may include a qualitative descriptor of the paced HS metric trend and the sensed HS metric trend. Alternatively, the concordance indicator may include a quantitative measure, such as a correlation between the paced HS metric trend and the sensed HS metric trend. A positive correlation between the ∥pS1∥ trend and the ∥sS1∥ trend, or between the pCTI trend and the sCTI trend indicates identical trends between the paced HS metric trend and the sensed HS metric trend (e.g., both are growth trends), and thus a higher level of concordance. In an example, the concordance indicator may include a ratio of a change in sensed S1 intensity (Δ∥sS1∥) to a change in paced S1 intensity (Δ∥pS1∥), or a ratio of a change in sensed CTI (ΔsCTI) to a change in paced CTI (ΔpCTI). A higher HS ratio corresponds to a higher level of concordance between the sensed HS metric trend and the paced HS metric trend.

At 550, one or more of a therapy adjustment indicator or a worsening cardiac contractility (WCC) indicator may be generated in response to the detected WHF event. The therapy adjustment indicator may be generated when the concordance indicator satisfies a first condition, and the WCC indicator may be generated when the concordance indicator satisfies a different second condition. The therapy adjustment indicator indicates that the detected WHF is attributed to reduced benefit of electrostimulation therapy under the present configuration and programming settings, and that the patient has preserved myocardial contractility. Therefore, further adjustment of electrostimulation therapy may provide additional benefit in rectifying WHF. The WCC indicator indicates that the detected WHF is attributed to pathological remodeling and degrading myocardial contractility, and mere reprogramming of pacing therapy may not achieve desired therapeutic benefits. Instead, medical therapies such as inotropic agents may be administered, in lieu of or in addition to electrostimulation therapy, to bolster myocardial contractility. Examples of generating the therapy adjustment indicator and the WCC indicator are discussed below, such as with reference to FIG. 6.

The therapy adjustment indicator and the WCC indicator may be output to a user (e.g., a clinician) or a process at 562, such as being displayed on a display of the output circuit 230. Trends of the paced and the sensed HS metrics, or trends of HS intensity ratio or CTI ratio, optionally along with other signals and intermediate results, may also be displayed. Additionally or alternatively, at 564, therapies may be delivered according to the therapy adjustment indicator, such as via the electrostimulator circuit 301. The therapy adjustment indicator may include recommendations for programming the electrostimulation therapy, such as adjustment of one or more of stimulation mode, stimulation site, or parameters controlling stimulation timing or stimulation strength. In an example, the reprogramming of the electrostimulation therapy may include activating electrostimulation at more pacing sites or switching to sites with late activation, changing the pacing mode to BiV or multisite pacing, reducing the AVD, increasing pacing amplitude or stimulation duration, among other programming changes. In some examples, at 564, drug therapies may be delivered according to the WCC indicator, such as by administering drugs such as inotropic agents to bolster myocardial contractility, under clinician intervention or via an automatically controlled drug infusion pump. In another example, autonomic modulation therapy such as vagal nerve stimulation may be delivered at 564 to improve cardiac contractility.

Figure 6:
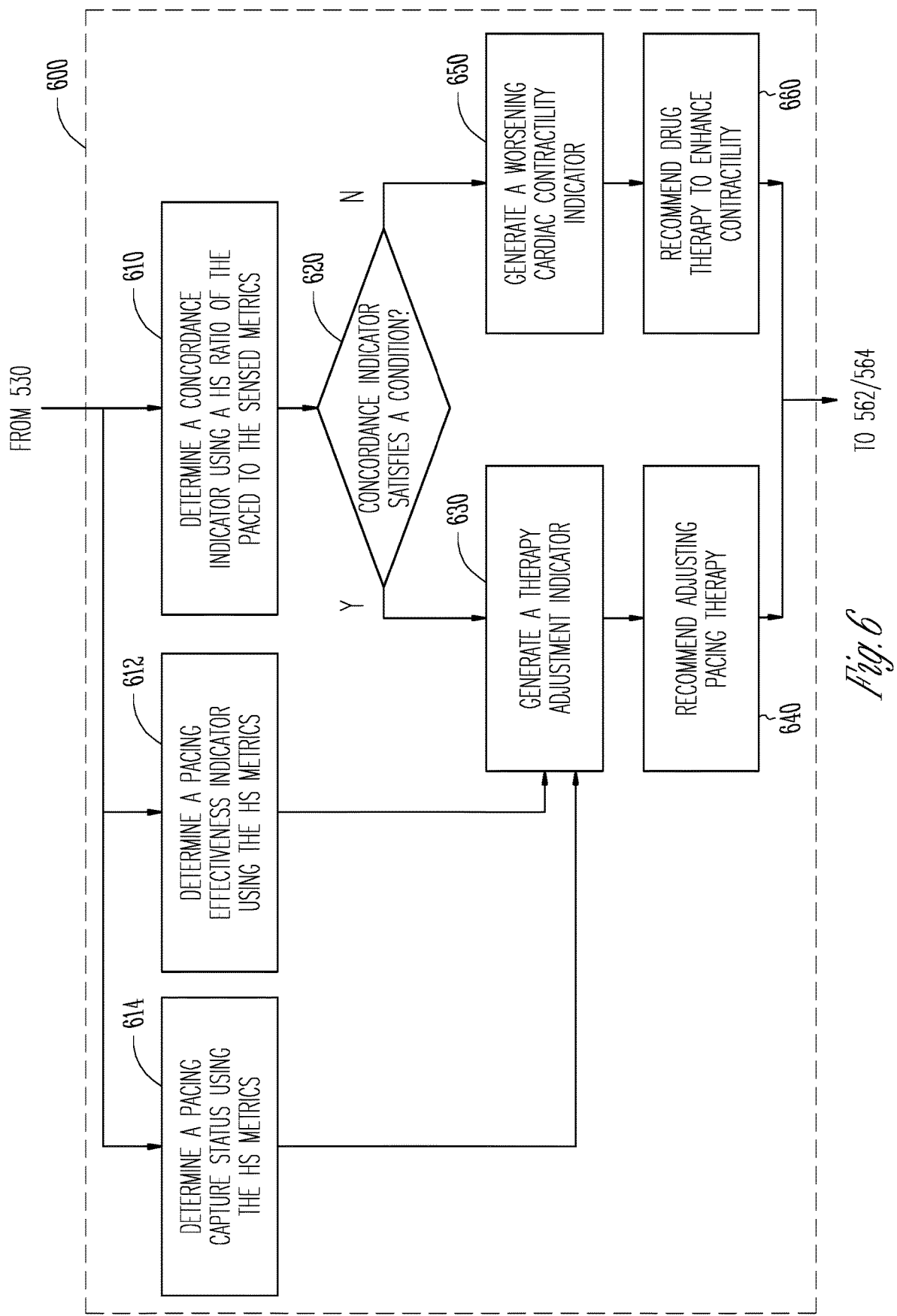
FIG. 6 illustrates generally an example of a method for identifying the causes of the WHF detection and making therapy recommendations accordingly.

FIG. 6 illustrates generally an example of a method 600 for identifying the causes of the WHF detection and making therapy recommendations accordingly. The method 600 may be embodiments of the portions of the method 500, such as steps 540-550, and may be implemented in, and executed by, the medical event detection system 200 or the feedback-controlled heart failure management system 300.

At 610, a concordance indicator may be generated using a ratio of a temporal change of the sensed. HS metric to a temporal change of the paced. HS metric. Examples of the HS ratio may include an S1 intensity ratio $\Delta\|sS1\|/\Delta\|pS1\|$, or a CTI ratio $\Delta sCTI/\Delta pCTI$. In some examples, at 610, the concordance indicator may be determined using a correlation between the paced HS metric trend and the sensed HS metric trend, such as a correlation between $\|pS1\|$ trend to $\|sS1\|$ trend, or between $\Delta pCTI$ trend and $\Delta sCTI$ trend.

At 620, the concordance indicator may be compared to one or more conditions to determine the causes of the WHF detected at 520. In an example, if at 620 the correlation between the paced HS metric trend and the sensed HS metric trend falls below a threshold, or if the HS ratio falls below a positive threshold value, then a low concordance between the paced and the sensed. HS metrics is indicated. The low concordance may suggest that the detected WHF is attributed to reduction in the benefit of electrostimulation therapy under the present configuration and programming settings. Accordingly, a therapy adjustment indicator may be generated at 630.

As illustrated in FIG. 6, information about a pacing effectiveness indicator (such as a CRT therapy effectiveness indicator) and a pacing capture status may be used in the process of generating the therapy adjustment indicator at 630. A pacing effectiveness indicator may be generated at 612 using the paced and the sensed HS metrics. In an example, the pacing effectiveness indicator may be determined using the paced S1 intensity ($\|pS1\|$) relative to the sensed S1 intensity ($\|sS1\|$), such as an intensity ratio $\|pS1\|/\|sS1\|$. An effective ventricular pacing may produce a stronger S1 than the sensed S1 in the absence of ventricular pacing, thus a larger intensity ratio $\|pS1\|/\|sS1\|$. The intensity ratio $\|pS1\|/\|sS1\|$ may be compared to a threshold to quantify the effectiveness of pacing. If the intensity ratio $\|pS1\|/\|sS1\|$ falls below the threshold TH, an indicator of ineffective pacing may be used to generate the therapy adjustment indicator at 630.

A capture status may be determined at 614 using the paced and the sensed HS metrics. In an example, the capture status may be determined using a measure of electromechanical coupling, such as an interval from the P wave on an ECG or an atrial pacing pulse, to S2 within a cardiac cycle. If the P–S2 interval is shorter than a threshold, or increases by a specific percentage over time, a loss of capture is indicated. The capture status may be used to generate the therapy adjustment indicator at 630.

At 630, a therapy adjustment indicator may be generated using one or more the concordance indicator, the pacing effectiveness indicator, or the capture status. As discussed above with reference to FIG. 5, the therapy adjustment indicator may include recommendation of programing of electrostimulation therapy such as by adjusting one or more of stimulation mode, stimulation site, or parameters controlling stimulation timing or stimulation strength. Recommendation for adjusting pacing therapy may be generated at 640. If the concordance indicator indicates a lack of concordance, or if intensity ratio $\|pS1\|/\|sS1\|$ falls below the threshold indicating reduced pacing effectiveness, or if loss of capture is indicated for ventricular pacing, or a combination of two or more of these conditions are satisfied, the a recommendation for activating electrostimulation at more pacing sites, switching to sites with late activation, changing the pacing mode to BiV or multisite pacing, reducing the AVD, increasing pacing amplitude or stimulation duration, among other programming changes may be produced at 640.

If at 620 the correlation exceeds a threshold or falls within a range indicating that both the paced and the sensed HS metrics decrease over time, or if the HS ratio exceeds a threshold, then a high degree of concordance between the paced and the sensed HS metrics is indicated. Accordingly, a WCC indicator may be generated at 650. A high concordance may suggest that the detected WHF is attributed to pathological remodeling and degrading myocardial contractility, and mere reprogramming of pacing therapy may not achieve desired therapeutic benefits. At 660, drug therapy, such as inotropic agents, may be recommended, in lieu of or in addition to electrostimulation therapy, to bolster myocardial contractility. In some examples, autonomic modulation therapy such as vagal nerve stimulation may be delivered to improve cardiac contractility.

In some examples, the paced HS metric, such as that generated at 530, may include a first paced HS metric corresponding to paced atrial contractions and a second paced HS metric corresponding to intrinsic atrial contractions. The first paced HS metric is generated using a portion of the first HS signal when both atrium and ventricle are paced, where the ventricular pacing is delivered at a paced AVD (pAVD) with respect to an atrial pacing pulse within the same cardiac cycle. The second paced HS metric is generated using a different portion of the first HS signal when the atrium is not paced, where the ventricular pacing is delivered at a sensed AVD (sAVD) with respect to an intrinsic atrial activation within the same cardiac cycle. At 610, a first concordance indicator between the first paced HS metric and the sensed. HS metric (e.g., a correlation or a ratio between $\|pS1\|$ corresponding to atrial pacing and $\|sS1\|$) and a second concordance indicator between the second paced HS metric and the sensed HS metric (e.g., a correlation or a ratio between $\|pS1\|$ corresponding to intrinsic atrial activation and $\|sS1\|$) may be generated. At 630, a therapy adjustment indicator for adjusting pAVD according to the first concordance indicator, or a therapy adjustment indicator for adjusting sAVD according to the second concordance indicator, may be generated. Respective recommendations may be produced at 640 for adjusting the pAVD or sAVD, optionally along with other therapy parameters.

Figure 7:
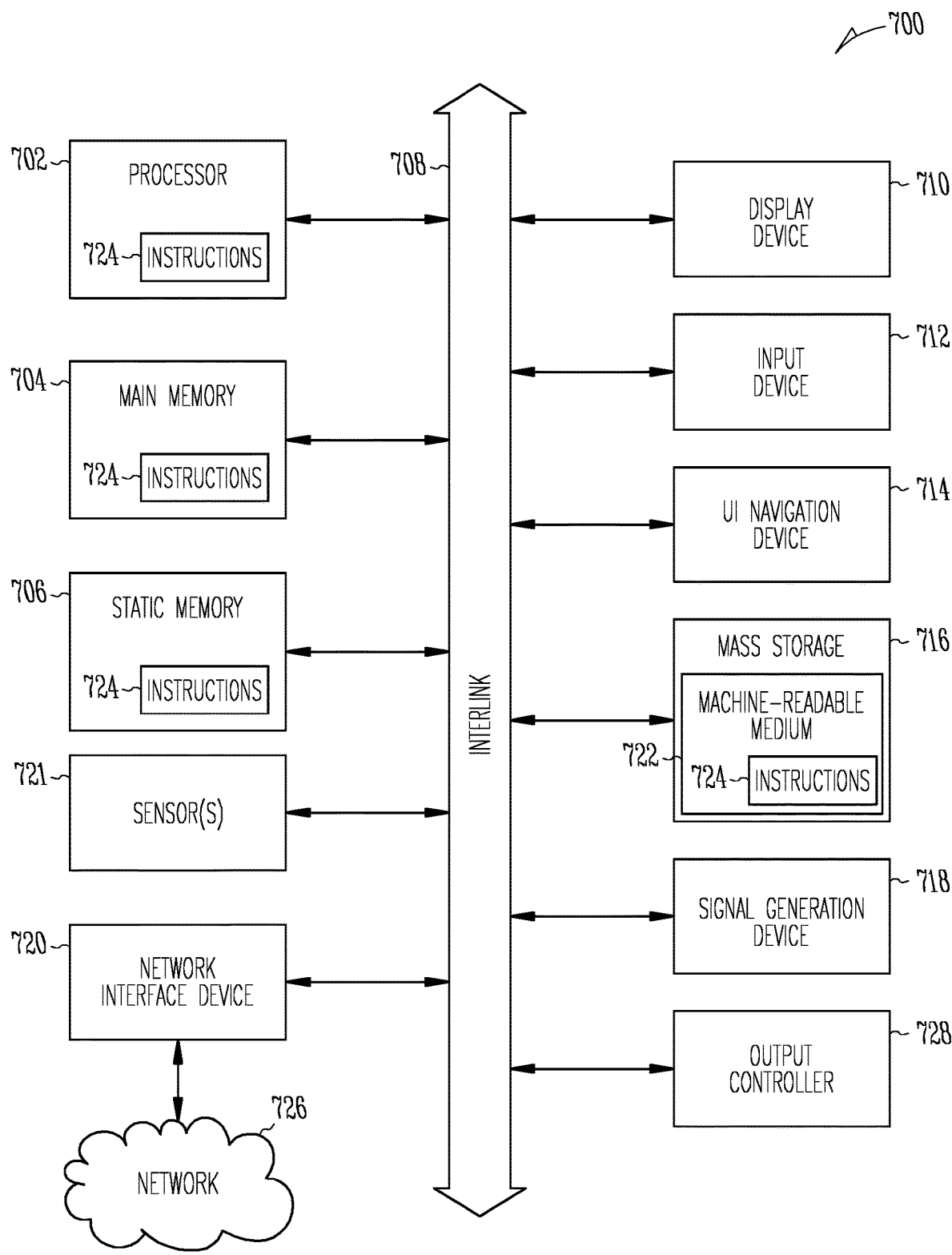
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (SIB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc. connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 724 may further be transmitted or received over a communication network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communication network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Sonic examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system, comprising:
   a receiver circuit configured to receive physiological information including a first heart sound (HS) signal corresponding to paced ventricular contractions and a second HS signal corresponding to intrinsic ventricular contractions; and
   a heart failure detector and analyzer circuit configured to:
      generate (1) a paced HS metric from the first HS signal and (2) a sensed HS metric from the second HS signal, the paced HS metric indicating cardiac contractility in response to paced ventricular contractions, the sensed HS metric indicating cardiac contractility in response to intrinsic ventricular contractions; and
      determine a worsening cardiac contractility indicator using a comparison between the paced HS metric and the sensed HS metric; and
   an output circuit configured to output the determined worsening cardiac contractility indicator to a user or a process of the system.

2. The system of claim 1, wherein the heart failure detector and analyzer circuit is configured to generate the worsening cardiac contractility indicator using a concordance between the paced and the sensed HS metrics.

3. The system of claim 2, wherein:
   the heart failure detector and analyzer circuit is configured to trend the paced HS metric and to trend the sensed HS metric over time, and to determine the concordance using the paced HS metric trend relative to the sensed HS metric trend; and
   the output circuit is configured to generate a therapy adjustment indicator when the concordance satisfies a first condition, and to generate the worsening cardiac contractility indicator when the concordance satisfies a different second condition.

4. The system of claim 2, wherein:
   the heart failure detector and analyzer circuit is configured to determine the concordance using a HS ratio of a temporal change of the sensed HS metric to a temporal change of the paced HS metric; and
   the output circuit is configured to generate a therapy adjustment indicator when the HS ratio satisfies a first condition, and to generate the worsening cardiac contractility indicator when the HS ratio satisfies a different second condition.

5. The system of claim 2, comprising an electrostimulator circuit configured to deliver cardiac pacing according to one or more pacing parameters, wherein the output circuit is configured to generate a therapy adjustment indicator for adjusting at least one of the one or more pacing parameters using the concordance between the paced and the sensed HS metrics.

6. The system of claim 5, wherein the electrostimulator circuit is configured to deliver ventricular pacing, and the output circuit is configured to generate the therapy adjustment indicator for adjusting timing of ventricular pacing using the concordance between the paced and the sensed HS metrics.

7. The system of claim 5, comprising a HS sensor circuit configured to sense the first HS signal when the electrostimulator circuit delivers ventricular pacing, and to sense the second HS signal when the electrostimulator circuit withholds ventricular pacing.

8. The system of claim 1, wherein the heart failure detector and analyzer circuit is configured to:
   generate the paced HS metric including a paced first sound (S1) intensity from the first HS signal during ventricular pacing; and
   generate the sensed HS metric including a sensed S1 intensity from the second HS signal in the absence of ventricular pacing.

9. The system of claim 8, wherein the heart failure detector and analyzer circuit is configured to determine a pacing effectiveness indicator using the paced S1 intensity relative to the sensed S1 intensity.

10. The system of claim 1, wherein the heart failure detector and analyzer circuit is configured to:
    generate the paced HS metric including a paced cardiac timing interval (CTI) from the first HS signal during ventricular pacing; and
    generate the sensed HS metric including a sensed CTI from the second HS signal in the absence of ventricular pacing.

11. The system of claim 1, wherein:
    the heart failure detector and analyzer circuit is configured to generate (1) a first paced HS metric from a first portion of the first HS signal corresponding to paced atrial contractions, and (2) a second paced HS metric from a different second portion of the first HS signal corresponding to intrinsic atrial contractions; and
    the output circuit is configured to generate a therapy adjustment indicator for adjusting one or more of timing of ventricular pacing relative to the atrial pacing, or timing of ventricular pacing relative to the intrinsic atrial contractions.

12. A system, comprising:
a receiver circuit configured to receive physiological information including a first heart sound (HS) signal corresponding to paced ventricular contractions and a second HS signal corresponding to intrinsic ventricular contractions;
a heart failure detector and analyzer circuit configured to:
generate (1) a paced HS intensity from the first HS signal and (2) a sensed HS intensity from the second HS signal, the paced HS intensity indicating cardiac contractility in response to paced ventricular contractions, the sensed HS intensity indicating cardiac contractility in response to intrinsic ventricular contractions; and
determine a worsening cardiac contractility indicator using a comparison between the paced HS intensity and the sensed HS intensity; and
a control circuit configured to adjust a therapy delivered to a patient based on the paced HS intensity and sensed HS intensity.

13. The system of claim 12, wherein the control circuit is configured to:
display information corresponding to the paced HS intensity and the sensed HS intensity; and
receive a therapy adjustment for adjusting the therapy provided to the patient.

14. A method for adjusting a heart failure therapy using a medical system, the method comprising:
receiving physiological information via a receiver circuit, the physiological information including a first heart sound (HS) signal corresponding to paced ventricular contractions and a second HS signal corresponding to intrinsic ventricular contractions;
generating (1) a paced HS metric from the first HS signal and (2) a sensed HS metric from the second HS signal via a heart failure detector and analyzer circuit, the paced HS metric indicating cardiac contractility in response to paced ventricular contractions, the sensed HS metric indicating cardiac contractility in response to intrinsic ventricular contractions;
determining a worsening cardiac contractility indicator using a comparison between the paced HS metric and the sensed HS metric via the heart failure detector and analyzer circuit; and
outputting the determined worsening cardiac contractility indicator to a user or a process.

15. The method of claim 14, wherein determining the worsening cardiac contractility indicator includes using a concordance between the paced and the sensed HS metrics.

16. The method of claim 15, comprising determining the concordance using a HS ratio of a temporal change of the sensed HS metric to a temporal change of the paced HS metric.

17. The method of claim 15, comprising:
adjusting one or more pacing parameters using the concordance between the paced and the sensed HS metrics; and
delivering cardiac pacing according to the adjusted one or more pacing parameters.

18. The method of claim 14, wherein generating the paced HS metric includes measuring a paced first sound (S1) intensity from the first HS signal during ventricular pacing, and generating the sensed HS metric includes measuring a sensed S1 intensity from the second HS signal in the absence of ventricular pacing.

19. The method of claim 14, wherein generating the paced HS metric includes:
measuring a paced cardiac timing interval (CTI) using the first HS signal during ventricular pacing; and
generating the sensed HS metric includes measuring a sensed CTI using the second HS signal in the absence of ventricular pacing.

20. The method of claim 14, comprising:
generating (1) a first paced HS metric from a first portion of the first HS signal corresponding to paced atrial contractions, and (2) a second paced HS metric from a different second portion of the first HS signal corresponding to intrinsic atrial contractions; and
generating a therapy adjustment indicator for adjusting one or more of timing of ventricular pacing relative to the atrial pacing, or timing of ventricular pacing relative to the intrinsic atrial contractions.

* * * * *